US010729365B2

(12) United States Patent
Beasley et al.

(10) Patent No.: US 10,729,365 B2
(45) Date of Patent: Aug. 4, 2020

(54) BIOMARKER SAMPLING IN THE CONTEXT OF NEUROMODULATION DEVICES, SYSTEMS, AND METHODS

(71) Applicant: Medtronic Ardian Luxembourg S.a.r.l., Luxembourg (LU)

(72) Inventors: Rudy Beasley, Santa Rosa, CA (US); Ayala Hezi-Yamit, Windsor, CA (US); Michele Lee Silver, Healdsburg, CA (US); Christopher W. Storment, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 268 days.

(21) Appl. No.: 15/424,575

(22) Filed: Feb. 3, 2017

(65) Prior Publication Data
US 2017/0202500 A1     Jul. 20, 2017

Related U.S. Application Data

(62) Division of application No. 13/791,751, filed on Mar. 8, 2013, now Pat. No. 9,597,018.
(Continued)

(51) Int. Cl.
*A61B 5/15*         (2006.01)
*A61B 5/157*        (2006.01)
(Continued)

(52) U.S. Cl.
CPC ............ *A61B 5/15* (2013.01); *A61B 5/14546* (2013.01); *A61B 5/15003* (2013.01);
(Continued)

(58) Field of Classification Search
CPC ........ A61B 18/1492; A61B 2018/0022; A61B 2018/00232; A61B 2018/00404;
(Continued)

(56) References Cited

U.S. PATENT DOCUMENTS

| 4,444,203 | A | * | 4/1984 | Engelman | ......... | A61M 25/0693 600/576 |
|---|---|---|---|---|---|---|
| 4,602,624 | A | | 7/1986 | Naples et al. | | |

(Continued)

FOREIGN PATENT DOCUMENTS

| CN | 101489624 | 7/2009 |
|---|---|---|
| EP | 1169976 | 1/2002 |

(Continued)

OTHER PUBLICATIONS

Extended European Search Report for Ep Application No. 17208077.2, dated Jun. 4, 2018, 11 pages.
(Continued)

*Primary Examiner* — Christopher Koharski
*Assistant Examiner* — Pamela M. Bays

(57) ABSTRACT

Methods for treating a patient using therapeutic renal neuromodulation and associated devices, systems, and methods are disclosed herein. One aspect of the present technology is directed to biomarker sampling in the context of neuromodulation devices, systems, and methods. Some embodiments, for example, are directed to catheters, catheter systems, and methods for sampling biomarkers that change in response to neuromodulation. A system can include, for example, an elongated shaft and a neuromodulation and sampling assembly having a neuromodulation and a sampling element.

19 Claims, 20 Drawing Sheets

Related U.S. Application Data

(60) Provisional application No. 61/608,625, filed on Mar. 8, 2012, provisional application No. 61/608,626, filed on Mar. 8, 2012, provisional application No. 61/746,528, filed on Dec. 27, 2012.

(51) Int. Cl.

| | |
|---|---|
| *A61B 5/20* | (2006.01) |
| *A61B 5/00* | (2006.01) |
| *A61N 7/02* | (2006.01) |
| *A61N 1/36* | (2006.01) |
| *A61N 1/40* | (2006.01) |
| *A61B 10/00* | (2006.01) |
| *A61B 18/14* | (2006.01) |
| *A61B 5/145* | (2006.01) |
| *A61N 1/05* | (2006.01) |
| *A61B 18/00* | (2006.01) |
| *A61B 18/18* | (2006.01) |
| *A61N 1/32* | (2006.01) |
| *G01N 33/68* | (2006.01) |
| *A61B 18/02* | (2006.01) |

(52) U.S. Cl.
CPC ............ *A61B 5/201* (2013.01); *A61B 5/4035* (2013.01); *A61B 5/4848* (2013.01); *A61B 5/6858* (2013.01); *A61B 18/1492* (2013.01); *A61N 1/05* (2013.01); *A61N 1/0551* (2013.01); *A61N 1/3605* (2013.01); *A61N 1/3606* (2013.01); *A61N 1/36135* (2013.01); *A61B 5/1405* (2013.01); *A61B 5/14503* (2013.01); *A61B 5/157* (2013.01); *A61B 5/150229* (2013.01); *A61B 5/150992* (2013.01); *A61B 5/20* (2013.01); *A61B 5/4836* (2013.01); *A61B 5/6851* (2013.01); *A61B 5/6852* (2013.01); *A61B 5/6853* (2013.01); *A61B 10/007* (2013.01); *A61B 10/0045* (2013.01); *A61B 18/02* (2013.01); *A61B 18/18* (2013.01); *A61B 2018/0022* (2013.01); *A61B 2018/00166* (2013.01); *A61B 2018/00214* (2013.01); *A61B 2018/00232* (2013.01); *A61B 2018/00279* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00875* (2013.01); *A61B 2018/0212* (2013.01); *A61N 1/32* (2013.01); *A61N 1/36007* (2013.01); *A61N 1/40* (2013.01); *A61N 7/02* (2013.01); *G01N 33/68* (2013.01); *G01N 2800/347* (2013.01)

(58) Field of Classification Search
CPC .. A61B 2018/00434; A61B 2018/0212; A61B 10/0045; A61B 2108/0051; A61B 2018/00511; A61B 5/15; A61B 5/4848; A61B 5/15003; A61B 5/201; A61B 5/4035; A61B 5/6858; A61B 5/14546; A61N 1/05; A61N 1/0551; A61N 1/3605; A61N 1/3606; A61N 1/36135
USPC ......................................................... 606/34
See application file for complete search history.

(56) References Cited

U.S. PATENT DOCUMENTS

| | | |
|---|---|---|
| 4,649,936 A | 3/1987 | Ungar et al. |
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,608,519 A * | 3/1997 | Gourley ................. G01N 15/10 250/461.2 |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster, Jr. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,160,296 B2 | 1/2007 | Pearson et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |

(56) References Cited

U.S. PATENT DOCUMENTS

| | | |
|---|---|---|
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,702,619 B2 | 4/2014 | Wang |
| 8,768,470 B2 | 7/2014 | Deem et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel et al. |
| 9,014,821 B2 | 4/2015 | Wang |
| 9,022,948 B2 | 5/2015 | Wang |
| 9,119,600 B2 | 9/2015 | Richardson et al. |
| 9,168,094 B2 | 10/2015 | Lee et al. |
| 9,179,973 B2 | 11/2015 | Nabutovsky et al. |
| 9,186,212 B2 | 11/2015 | Nabutovsky et al. |
| 9,295,842 B2 | 3/2016 | Ghaffari et al. |
| 9,314,300 B2 | 4/2016 | Nabutovsky et al. |
| 9,375,154 B2 | 6/2016 | Wang |
| 9,427,283 B2 | 8/2016 | Nabutovsky et al. |
| 9,427,579 B2 | 8/2016 | Fain et al. |
| 9,554,850 B2 | 1/2017 | Lee et al. |
| 9,579,030 B2 | 2/2017 | Scheuermann et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0153379 A1 | 7/2005 | Hoon et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0135875 A1 | 6/2007 | Demarais et al. |
| 2007/0265687 A1 | 11/2007 | Deem et al. |
| 2008/0057590 A1 | 3/2008 | Urdea et al. |
| 2008/0140000 A1* | 6/2008 | Shuros ............... A61N 1/36007 604/96.01 |
| 2008/0319513 A1 | 12/2008 | Pu et al. |
| 2009/0024195 A1* | 1/2009 | Rezai .................. A61N 1/0558 607/116 |
| 2009/0036948 A1 | 2/2009 | Levin et al. |
| 2009/0105605 A1* | 4/2009 | Abreu .................. A61B 5/0008 600/549 |
| 2009/0258002 A1* | 10/2009 | Barrett ................. C12Q 1/6886 424/130.1 |
| 2010/0036451 A1* | 2/2010 | Hoffer ................. A61N 1/0558 607/42 |
| 2010/0069888 A1 | 3/2010 | Solomon |
| 2010/0086948 A1 | 4/2010 | Gold et al. |
| 2010/0087716 A1 | 4/2010 | Nashed |
| 2010/0114244 A1 | 5/2010 | Manda et al. |
| 2010/0137860 A1 | 6/2010 | Demarais et al. |
| 2010/0137952 A1 | 6/2010 | Demarais et al. |
| 2010/0166739 A1 | 7/2010 | Chancellor et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0331833 A1 | 12/2010 | Maschke et al. |
| 2011/0060324 A1 | 3/2011 | Wu et al. |
| 2011/0112400 A1 | 5/2011 | Emery et al. |
| 2011/0152759 A1 | 6/2011 | Clymer et al. |
| 2011/0160644 A1 | 6/2011 | Dacey, Jr. et al. |
| 2011/0178570 A1 | 7/2011 | Demarais |
| 2011/0184337 A1 | 7/2011 | Evans et al. |
| 2011/0208096 A1* | 8/2011 | Demarais ............... A61F 7/123 601/3 |
| 2011/0270120 A1 | 11/2011 | McFarlin et al. |
| 2011/0306851 A1 | 12/2011 | Wang |
| 2012/0029504 A1 | 2/2012 | Afonso et al. |
| 2012/0065554 A1* | 3/2012 | Pikus ................... A61B 18/02 601/2 |
| 2012/0116383 A1 | 5/2012 | Mauch et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0296232 A1 | 11/2012 | Ng |
| 2012/0296329 A1 | 11/2012 | Ng |
| 2013/0085489 A1 | 4/2013 | Fain et al. |
| 2013/0123778 A1 | 5/2013 | Richardson et al. |
| 2013/0172878 A1 | 7/2013 | Smith |
| 2013/0178750 A1 | 7/2013 | Sheehan et al. |
| 2013/0218029 A1 | 8/2013 | Cholette et al. |
| 2013/0237948 A1 | 9/2013 | Donders et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0018656 A1 | 1/2015 | Min et al. |
| 2015/0025524 A1 | 1/2015 | Nabutovsky |
| 2015/0112329 A1 | 4/2015 | Ng |
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |

(56) References Cited

U.S. PATENT DOCUMENTS

| | | |
|---|---|---|
| 2015/0289770 A1 | 10/2015 | Wang |
| 2015/0289929 A1 | 10/2015 | Toth et al. |
| 2015/0366609 A1 | 12/2015 | Richardson et al. |
| 2016/0000345 A1 | 1/2016 | Kobayashi et al. |
| 2016/0029960 A1 | 2/2016 | Toth et al. |
| 2016/0038028 A1 | 2/2016 | Buelna et al. |
| 2016/0081744 A1 | 3/2016 | Wang |
| 2016/0106498 A1 | 4/2016 | Highsmith et al. |
| 2016/0184010 A1 | 6/2016 | Nabutovsky et al. |
| 2016/0213262 A1 | 7/2016 | Ghaffari et al. |
| 2016/0213424 A1 | 7/2016 | Ghaffari et al. |
| 2016/0324572 A1 | 11/2016 | Gross et al. |
| 2016/0331451 A1 | 11/2016 | Nabutovsky et al. |
| 2016/0331453 A1 | 11/2016 | Fain et al. |
| 2016/0374568 A1 | 12/2016 | Wang |
| 2017/0215950 A1 | 8/2017 | Gross et al. |

FOREIGN PATENT DOCUMENTS

| | | |
|---|---|---|
| EP | 2316371 | 5/2011 |
| EP | 2594193 | 5/2013 |
| EP | 2613704 | 7/2013 |
| EP | 2747691 | 7/2014 |
| EP | 2797535 | 11/2014 |
| EP | 2852339 | 4/2015 |
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3011899 | 4/2016 |
| EP | 3028628 | 6/2016 |
| EP | 3089686 | 11/2016 |
| EP | 2709517 | 1/2017 |
| JP | H08504531 | 5/1996 |
| JP | H1071037 | 3/1998 |
| JP | 2001518808 | 10/2001 |
| JP | 2005278739 | 10/2005 |
| JP | 2008515544 | 5/2008 |
| JP | 2009539565 | 11/2009 |
| JP | 2010162163 | 7/2010 |
| JP | 2010533513 | 10/2010 |
| JP | 2011505929 | 3/2011 |
| WO | WO-2014091328 | 7/1989 |
| WO | WO-1994007446 | 4/1994 |
| WO | WO-1995025472 | 9/1995 |
| WO | WO-1995031142 | 11/1995 |
| WO | WO-1997036548 | 10/1997 |
| WO | WO-1998042403 | 10/1998 |
| WO | WO-1999000060 | 1/1999 |
| WO | WO-001022897 | 4/2001 |
| WO | WO-2001070114 | 9/2001 |
| WO | WO-2003022167 | 1/2003 |
| WO | WO-2003082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008003058 | 1/2008 |
| WO | WO-2008049084 | 4/2008 |
| WO | WO-2010078175 | 7/2010 |
| WO | WO-2011089935 | 7/2011 |
| WO | WO-2012024543 | 2/2012 |
| WO | WO-2012033974 | 3/2012 |
| WO | WO-2012068471 | 5/2012 |
| WO | WO-2012158864 | 11/2012 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014091401 | 6/2014 |
| WO | WO-2014149550 | 9/2014 |
| WO | WO-2014149552 | 9/2014 |
| WO | WO-2014149553 | 9/2014 |
| WO | WO-2014149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014158708 | 10/2014 |
| WO | WO-2014158713 | 10/2014 |
| WO | WO-2014163990 | 10/2014 |
| WO | WO-2014179768 | 11/2014 |
| WO | WO-2014182946 | 11/2014 |

OTHER PUBLICATIONS

Allen, E.V., Sympathectomy for essential hypertension, Circulation, 1952, 6:131-140.

Bello-Reuss, E. et al., "Effects of Acute Unilateral Renal Denervation in the Rat," Journal of Clinical investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephroi Diai Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935:443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

(56) References Cited

OTHER PUBLICATIONS

Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain" Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation", Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coroary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Caridiac Ablation Controller & Accessries, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://ciinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.

Pieper, et ai., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Associatio3766merica Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.corn/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-06-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatrnent-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech businesseport, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.

(56) References Cited

OTHER PUBLICATIONS

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension," St. Jude Medical, Inc., 2012, 12 pages.
"Vessix Renal Denervation System: So Advanced it's Simple," [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emillio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnvervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardi-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry," EuroIntervention, vol. 9, 2013, 9 pages.
Brosky, John, "EuroFCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al,, "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pages.
Demarais et al., Reexamination U.S. Appl. No. 95/002,110 now U.S. Pat. No. 7,717,948 filed Aug. 29, 2012.
Demarais et al., Reexamination U.S. Appl. No. 95/002,253 now U.S. Pat. No. 8,131,371 filed Sep. 13, 2012.
Demarais et al., Reexamination U.S. Appl. No. 95/002,292 now U.S. Pat. No. 8,175,711 filed Sep. 14, 2012.
Demarais et al., Reexamination U.S. Appl. No. 95/002,335 now U.S. Pat. No. 8,150,520 filed Sep. 14, 2012.
Demarais et al., Reexamination U.S. Appl. No. 95/002,356 now U.S. Pat. No. 8,150,519 filed Sep. 14, 2012.
Demarias et al., Reexamination U.S. Appl. No. 95/002,327 now U.S. Pat. No. 8,145,317 filed Sep. 14, 2012.
Dibona, G.F. "Sympathetic nervous system and kidney in hypertension." Nephrol and Hypertension, 11: 197-200 (2002).
Dibona, G.F., et al. "Neural control of renal function." Physiol Rev. 77:75-197 (1997).
Doumas, Michael et al., "Renal Nerve Ablation for Resistant Hypertension: The Dust Has Not Yet Settled." The Journal of Clinical Hypertension. 2014; vol. 16, No. 6, 2 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resitant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet The Tech Duo That's Revitalizing The Medical Device Industry." FAST Company, Apr. 15, 2013. 6:00 AM, 17 pages, <http://www.fastcompany.com/3007845/meet-tech-duo-thats-revitalizing-medical-device-industry>.
Golwyn, D. H., Jr., et al., "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid remal tumor." *Am. J. Roentgenol*,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages. <http://97waterlooroad.wordpress.com/2012/11/12/medtronic-awarded-industrys-highest-honour-for-remal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Levin et al. Reexamination U.S. Appl. No. 95/002,209 now U.S. Pat. No. 8,150,518 filed Sep. 13, 2012.
Levin et al., Reexamination U.S. Appl. No. 95/002,233 now U.S. Pat. No. 8,131,372 flied Sep. 13, 2012.
Levin et al., Reexamination U.S. Appl. No. 95/002,243 now U.S. Pat. No. 7,162,303 filed Sep. 13, 2012.
Levin et al., Reexamination U.S. Appl. No. 95/002,336 now U.S. Pat. No. 7,647,115 filed Sep. 14, 2012.
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.

(56) References Cited

OTHER PUBLICATIONS

Messerli, Franz H. et al. "Renal Denervation for Resistant Hypertension: Dead or Alive?" Healio: Cardiology today's Intervention, May/Jun. 2014, 2 pages.

Millard, F. C., et al, "Renal Embolization for ablationof function in renal failure and hypertension." Postgraduate Medical Journal, 65, 729-734, (1989).

Miller, Reed, "Finding a Future for Renal Denervation With Better Controlled Trials." Pharma & Medtech Business Intelligence, Article # 01141006003, Oct. 6, 2014, 4 pages.

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShotTM renal denervation system from Covidien." EuroIntervention, vol. 8, 2013, 4 pages.

Ormiston, Johnn et al., "Renal denervation for resistant hypertension using an irrigated rediofrequency balloon: 12-month results from the Renal Hypertension Ablation System (RHAS) trial." EuroIntervention, vol. 9, 2013, 5 pages.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt is the Beginning of Wisdom)", Circulation Research, 2014; 115: 211-214.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter Ablation of Cardiac Autonomic Nerves for Prevention of Vagal Atrial Fibrillation." Circulation, 102:2774-2780 (2000).

Schlaich, Markus et al., "Renal Denervation in Human Hypertension: Mechanisms, Current Findings, and Future Prospect." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Smithwick et al., "Splanchnicectomy for essential hypertension." J. Am. Med. Assn. 152:16 (1953), pp. 1501-1504.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversable renal denervation on haemodynamic and excretory functions on the ipsilateral and contralateral kidney in the cat." Hypertension, 4: 181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricuiar pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Valente, J.F. "Laparoscopic renal denervation for intractable ADPKD-related pain." Nephrol Dial Transplant, 16: 160 (2001).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Abruzzo, Provvidenza et al., "Oxidative stress in the denervated muscle," Free Radical Research, vol. 44, No. 5, 2010, 563-576.

Amsellem S. et al., Cubilin is Essential for Albumin Reabsorption in the Renal Proximal Tubule,' J Am Soc Nephril, vol. 21, 2010,1859-1867.

Andres, Vicente, "Control of vascular cell pro;iferation and migration by cyclin-dependent kinase signalling: new perspectives and therapeutic potential," Cardiovascular Research; vol. 63, 2004, 11 pages.

Ankiri, R. et al., "In-vivo Tumor detection using diffusion reflection measurements of targeted gold nanorods—a quantitative study," Biophotonics, 2012, 11 pages.

Bengatta, S. et al., "MMP9 and SCF Protect from Apoptosis in Acute Kidney Injury," J Am Soc Nephril, vol. 20, 2009, 787-797.

Bhattacharya, S. et al. "Role of p38 Protein Kinase in the Ligand-independent Ubiquitination and Down-regulation of the IFNAR1 Chain of Type I Interferon Receptor," The Journal of Biological Chemistry, vol. 286 No. 25, 2011, 22069-22076.

Bisoffi, M. et al., "Detection of viral bioagents using a shear horizontal surface acoustic wave biosensor," Biosensors and Bioelectronics, vol. 23, 2008, 7 pages.

Centi et al., "Strategies for electrochemical detection in immunochemistry," Bioanalysis, vol. 1. No. 7, 2009, 21 pages.

Dange, M. et al., "Each Conserved Active Site Tyr in the Three Subunits of Human Isocitrate Dehydrogenase Has a Different Function," The Journal of Biological Chemistry, vol. 285, No. 27, 2010, 6 pages.

Darisipudi, M. et al., "Dual Blockade of the Homeostatic Chemokine CXCL 12 and the Proinflammatory Chemokine CCL2 has Addictive Protective Effects on Diabetic Kidney Disease," The American Journal of Pathology, vol. 179, No. 1, 2011, 9 pages.

Dhruvajyoti, Roy et al., ""Seeing and Counting" individual antigens Captured on a Microarrayed Soit with Force-Based Atomic Force Microscopy," Anal. Chem. vol. 82, 2010 6 pages.

Dikow, Ralf et al., "In Renal Transplants With Delayed Graft Function Chemokines and Chemokine Receptor Expression Predict Long-Term Allograft Function," Transplantation, vol. 90, 2010. 71-776.

Dinish, U. et al., "Highly sensitive SERS detection of cancer proteins in low sample volume using hollow core photonic crystal fiber," Biosens, Bioelecton, 2012, 6 pages.

Dorr et al., "Soluble fms-Like Tyrosine Kinase-1 and Endothelial Adhesion Molecules (Intercellular Cell Adhesion Molecule-1 and Vascular Cell Adhesion Molecule-1) as Predictive Markers for Blood Pressure Reduction After Renal Sympathetic Denervation." Hypertension, 2014, 63, pp. 984-990.

(56) References Cited

OTHER PUBLICATIONS

Ford, M. et al., "Expression of fibroblast growth factors and their receptors in rat glomeruli," Kidney International, vol. 51, 1997, 10 pages.
Fragiadaki, Maria et al., "Interstitial fibrosis is associated with increased COL1A2 transcription in AA-injured renal tubular epithelial cells in vivo," Matrix Biology, vol. 30, 2011, 396-403.
Frostick, S. et al., "Schwann Cells, Neurotrophic Factors, and Peripheral Nerve Regeneration," Microsurgery, vol. 18, 1998, 9 pages.
Gaikinad, A. et al., "Epigenetic changes and alteration of Fbn1 and Col3A1 gene expression under hyperglycaemic and hyperinsulinaemic conditions," Biochem. J., vol. 432, 2010, 10 pages.
Green, H., et al., "Development of ERK Activity Sensor, an in vitro, FRET-based sensor of Extracellulat Regulated Kinase activity," BMC Chemical Biology, vol. 5, No. 1, 2005, 8 pages.
Grishman, Ellen et al., "Toll-like receptors, the NLRP3 inflammasome, and interleukin-1β in the development and progression of type 1 diabetes," Pediatric Research, vol. 71, No. 6, 2012, 7 pages.
Heberlein, Annemarie et al., BDNF plasma levels decrease during benzodiazepine withdrawal in patients suffering from comorbidity of depressive disorder and benzodiazepine dependence, Psychopharmacology, vol. 209, 2010, 3 pages.
Hervas, M. et al., "Electrochemical immunosensing on board microfluidic chip platforms," Trends in Analytical Chemistry, vol. 31, 2012, 20 pages.
Higgins, J, et al., "Gene Expression in the Normal Adult Human Kidney Assessed by Complementary DNA Microarray," Molecular Biology of the Cell, vol. 15, 2004, 649-656.
Hirst, E., "Bond-rupture immunosensors—A review," Biosensors and Bioelecronics, vol. 23, 2008, 10 pages.
Horke, S. et al., "Paraoxonase-2 Reduces Oxidative Stress in Vascular Cells and Decreases Endoplasmic Reticulum Stress—Induced Caspase Activation," Circulation, vol. 115, 2007, 11 pages.
Ihling, C. et al., "Endothelin-1 and Endothelin Converting Enzyme-1 in Human Atherosclerosis—Novel Targets for Pharmacotherapy in Atherosclerosis," Current Vascular Pharmacology, vol. 2, 2004, 10 pages.
Jacobs, C. et al., "Review: Carbon nanotube based electrochemical sensors for biomolecules," Analytical Chimica Acta, vol. 662, 2010, 23 pages.
Jin, Xinghua et al., "Delineation of apoptotic genes for synergistic apoptosis of lexatumumab and anthracyclines in human renal cell carcinoma cells by polymerase chain reaction array," Anti-Cancer Drugs, vol. 23, No, 4, 2012, 10 pages.
Johnson, B. et al., "Biosensing using dynamic-mode cantilever sensors: A revie " Biosensors and Bioelectronics, vol. 32, 2012, 18 pages.
Kasuno, Kenji et al., "Clinical Application of Urinary Redox Regulating Protein," Thioredoxin, Rinsho Byori, vol. 59, 2011, 189-195.
Kerr, Heather et. al,, "Complement-mediated injury and protection of enforheliurn: Lessons from atypical haemolytic uraemic syndrome," Immunobiology, vol. 217, 2012, 195-203.
Kinoshita, Yukiko et al., "Angiotensin II type I receptor blockade suppresses glomerular renin-angiotensin system activation,; oxidative stress, and progressive glomerular injury in rat anti-glomerular basement membrane; glomerulonephritis," Translational Research, vol. 158, No. 4, 2011, 15 pages.
Klosterhalfen, B. et al., "Influence of Heat Shock Protein 70 and Metallothionein Induction by Zinc-bis-(DL-Hydrogenaspartate) on the Release of Inflammatory Mediators in a Porcine Model of Recurrent Endotoxemia." Biochemical Pharmacology, vol. 52, 1996, 1201-1210.
Kopp, "Endothelin in the Control of Renal Sympathetic Nerve Activity," Contrib Nephrol. Basel, Karger, vol. 172, 2011, 107-119.
Kopp, Ulla C. et al., "Impaired Interaction Between Efferent and Afferent Renal Nerve Activity in SHR Involves Increased Activation of α2-Adrenoceptors," vol. 57, 2011, 640-647.

Kourtzelis, L., et al., "Complement anaphylatoxin C5a contributes to hemodialysis-associated thrombosis," Blood, 116, No. 4, 2010 9 pages.
Krukoff, Teresa L. et al., "Effects of renal denervation and reinnervation on ganglionic gene; expression of neurotransmitter proteins and c-fos in rat," Molecular Brain Research, vol. 19, 1993, 6 pages.
Lan, Hui Yao, Transforming growth factor-β/Smad signalling in diabetic nephropathy, Clinical and Experimental Pharmacology and Physiology, vol. 39, 2012, 731-738.
Lantero, A. et al., "Transforming Growth Factor-β in Normal Nociceptive Processing and Pathological Pain Models," Mol Neurobiol, vol. 45, 2012, 76-86.
Lechner, Stefan et al., "Regulation of neuronal ion channels via P2Y receptors," Purinergic Signalling, vol. 1, 2004, 31-41.
Lee, Y. et al., "Fibromodulin Suppresses Nuclear Factor-κB Activity by Inducing the Delayed Degradation of IKBA via a JNK-dependent Pathway Coupled to Fibroblast Apoptosis," The Journal of Biological Chemistry, vol. 286, No. 8, 2011, 9 pages.
Leguillon-Buffello, D. et al., "An Alternative Quantitative Acoustical and Electrical Method for Detection of Cell Adhesion Process in Real-Time," Biotechnology and Bioengineering, vol. 108, No. 4, 2011, 16 pages.
Leonard, M., et al., "Reoxygenation-specific activation of the antioxidant transcription factor Nrf2 mediates cytoprotective gene expression in ischemia-reperfusion injury," The FASEB Journal, vol. 20, 2006, 3 pages.
Liang, W., et al., "A novel microfluidic immunoassay system based on electrochemical immunosensors: An application for the detection of NT-proBNP in whole blood," Biosensors and Bioelectronics, vol. 31, 2012, 6 pages.
Liu, Bin et al., "Role of cyclooxygenase-1-mediated prostacyclin synthesis in endothelium-dependent vasoconstrictor activity of porcine interlobular renal arteries," Am J Physiol Renal Physiol, vol. 302, 2012, F1133-F1140.
Liu, Y. et al., "BID Binds to Replication Protein A and Stimulates ATR Function following Replicative Stress," Molecular and Cellular Biology, vol. 31, No. 21, 2011, 12 pages.
Liu, Yarixin et al., "A novel SNP of the ATP1A1 gene is associated with heat tolerance traits in dairy cows," vol. 38, 2011, 83-88.
Liu, Ying et al., "Induction of KLF4 in response to heat stress," Cell Stress & Champerones, vol. 11, No. 4, 2006, 379-389.
Liu, Yong et al., "Renal Medullary MicroRNAs in Dahl Salt-Sensitive Rats: miR-29b Regulates Several Collagens and Related Genes," Hypertension, vol. 55, 2010, 974-982.
Lloyd-Burton, S, et al., "SPARC-Like 1 (SC1) is a Diversely Expressed and Developmentally Regulated Matricellular Protein That Does Not Compensate for the Absence of SPARC in the CNS," The Journal of Comparative Neurology: Research in Systems Neuroscience, vol. 520, 2012, 2575-2590.
Lo, Denise et al., "Chemokines and their Receptors in Human Renal Allotransplantation," Transplantation, Author manuscript; available in PMC, 2012, 14 pages.
Longley, C. D. et al., "Proportions of Renal and Splenic Postganglionic Sympathetic Populations Containing Galanin and Dopamine Beta Hydroxylase," Neuroscience, vol. 55, No. 1, 1993, 9 pages.
Lu, X. et al., "The Role of Heat Shock Protein (HSP) in Atherosclerosis: Pathophysiology; and Clinical Opportunities," Current Medicinal Chemistry, vol. 17, 2010, 957-973.
Luo, Lin, "Gene expression profiles of laser-captured adjacent neuronal subtypes," Nature Medicine, vol. 5, No. 1, 1999, 6 pages.
Ma, Frank, et al., "TGF-β1-activated kinase-1 regulated inflammation and fibrosis in the obstructed kidney," Am J. Physiol Renal Physiol, vol. 300, 2011, 12 pages.
Maeshima, A. et al., "Activin A: Autocrine Regulator of Kidney Development and Repair," Endocrine Journal, vol. 55, No. 1, 2008 9 pages.
Maity, Tapan et al., "Distinct, Gene Specific Effect of Heat Shock on Heat Shock Factor-1 Recruitment and Gene Expression of CXC Chemokine Genes," Cytokine, Author manuscript, available in PMC, 2012, 14 pages.

(56) References Cited

OTHER PUBLICATIONS

Mas, Valeria et al., "Gene Expression Patterns in Deceased Donor Kidneys Developing Delayed Graft Function After Kidney Transplantation," Transplantation, vol. 85, No. 4, 2008, 10 pages.
Mazanowska, O. et al, "Imbalance of Metalloproteinase/Tissue Inhibitors of Metalloproteinase System in Renal Transplant Recipients With Chronic Allograft Injury." Transplantation Proceedings, vol. 43, 2011, 4 pages.
Messina, G., et al., "Microfluidic immunosensor design for the quantification of interleukin-6 in human serum samples," Analytical Biochemistry, vol. 380, 2008, 6 pages.
Metters, J. et al., "New directions in screen printed elctroanalytical sensors: an overview of recent developments," Analyst, vol. 136, 2011, 10 pages.
Musial K., et al., "Heat shock proteins in chronic kidney disease," Journal of the International Pediatric Nephrology Association, 2010, 9 pages.
Nakaya, R. et al., "Identification of proteins that may directly interact with human RPA," J. Biochem, vol. 148, No. 5, 2010, 9 pages.
Nath, N. et al., "Evanescent wave fibre optic sensor for detection of L. donovani specific antibodies in sera of kala azar patients," Biosensors & Bioelectronics, 1996, 8 pages.
Obeidat, Motaz A., et al., "Post-transplant nuclear renal scans correlate with renal injury; biomarkers and early allograft outcomes," Nephrol Dial Transplant, vol. 26, 2011, 8 pages.
Orellana G. et al., "New Trends in Fiber-Optic Chemical and Biological Sensors," Current Analytical Chemistry, vol. 4, 2008, 23 pages.
Pache, G. et al., "Upregulation of Id-1 via BMP-2 receptors induces reactive oxygen species in podocytes," Am J Physiol Renal Physiol, vol. 291, 2006, 9 pages.
Panini, N. et al., "Integrated microfluidoc systems with an immunosensor modified with carbon nanotubes for detection of prostate specific antigen (PSA) in human serum samples," Biosensors and Bioelectronics, vol. 23, 2008, 7 pages.
Paulis, L. et al., "Novel therapeutic targets for hypertension," Nature Reviews: Cardiology, vol. 7, 2010, 11 pages.
Pereira, Rui et al., "Neutrophil and monocyte activation in chronic kidney disease patients under hemodialysis and its relationship with; resistance to recombinant human erythropoietin and to the hemodialysis procedure," Hemodialysis International, vol. 14, 2010, 7 pages.
Ransom, Richard F. et al., "Differential proteomic analysis of proteins induced by gluecocorticoids in cultured murine podocytes," Kidney International, vol. 67, 2005, 1275-1285.
Reich, Heather N. et al., "Molecular Markers of Injury in Kidney Biopsy Specimens of Patients with Lupus Nephritis," The Journal of Molecular Diagnostics, vol. 13, No. 2, 2011, 9 pages.
Romanenko, Alina et al., "p16INK4A and p15INK4B Gene Alteration Associated; with Oxidative Stress in Renal Cell Carcinomas; After the Chernobyl Accident (Pilot Study)," Diagnostic Molecular Pathology, vol. 11, No. 3, 2002, 163-169.
Ruotsalainen, V. et al., "Nephrin is specifically located at the slit diaphragm of glomerular podocytes," Proc. Natl. Acad. Sci. USA, vol. 96, 1999, 6 pages.
Rusling, J. et al., "Measurement of biomarker proteins for point-of-care early detection and monitoring of cancer," Analyst, Author manuscript, available in PMC, 2010, 31 pages.
Rusnati, M. et al., "Exploiting Surface Plasmon Resonance (SPR) Technology for the Identification of Fibroblast Growth Factor-2 (FGF2) Antagonists Endowed with Antiangiogenic Activity," Sensors, vol. 9, 2009, 33 pages.
Sadik, O. et al., "Status of biomolecular recognition using electrochemical techniques," Biosensors and Bioelectronics, vol. 24, 2009, 17 pages.
Saito, S. et al., "Analysis of glial cell line-derived neurotrophic factor-inducible zinc finger protein 1 expression in human diseased kidney," Human Pathology, col. 42, 2011, 11 pages.

Sataranatarajan, K. et al., "Regulation of Elongation Phase of mRNA Translation in Diabetic Nephropathy," The American Journal of Pathology, vol. 171, No. 6, 2007, 10 pages.
Sigdel, Tara K. et al., "Shotgun Proteomics Identifies Proteins Specific for Acute Renal; Transplant Rejection," Proteomics Clin Appl. Author manuscript; available in PMC 2010, 27 pages.
Snigdha, Shikha et al., "Caspase-3 activation as a bifurcation point between plasticity and cell; death," Neurosci Bull, vol. 28, No. 1, 2012, 11 pages.
Soleimani, M., "Dietary fructose, salt absorption arid hypertension in; metabolic syndrome: towards a new paradigm," Acta Physiol, vol. 201, 2011, 55-62.
Sonna, L. et al., "Molecular Biology of Thermoregulation Invited Review: Effects of heat and cold stress on mammalian gene expression," J Appl Physiol, vol. 92, No. 1725, 2002, 17-42.
Struckmann, Kirsten et al., "Impaired Expression of the Cell Cycle Regulator BTG2 is Common in Clear Cell Renal Cell Carcinoma," Cancer Res, vol. 64, 2004, 1632-1638.
Su, Y. et al., "Chromatic immunoassay based on polydiacetylene vesicles," Colloids and Surfaces B: Biointerfaces, vol. 38, 2004, 5 pages.
Sun, A. et al., "Sensitive label-free electrochemical immunoassay based on a redox matrix of gold nanoparticles/Azure I/multi-wall carbon nanotubes composite," Biochemical Engineering Journal, vol. 57, 2011, 6 pages.
Sun, Dong et al., "Thrombospondin-1 Short Hairpin RNA Suppresses Tubulointerstitial Fibrosis in the Kidney of Ureteral Obstruction by Ameliorating Peritubular Capillary Injury," Kidney Blood Press Res, vol. 35, 2012, 6 pages.
Tiniakos, D. et al, "Ontogeny of intrinsic innervation in the human kidney," Anat Embryol, vol. 209, 2004, 7 pages.
Todorov, Vladimir et al., "Differential Regulation of Cathepsin B and Prorenin Gene Expression in Renal Juxtaglomerular Cells," Kidney Blood Press Res, vol. 24, 2001, 4 pages.
Trimarchi, Hernan et al., "Proteinuria: an ignored marker of inflammation and cardiovascular disease in chronic hemodialysis," International Journal of Nephrology and Renovascular Disease, vol. 5, 2012, 7 pages.
Vivekanandan, A. et al., "Urine Glycoprotein Profile Reveals Novel Markers for Chronic Kidney Disease," International Journal of Proteomics, 2011, 18 pages.
Waalkes et al., "Fibronectin 1 mRNA expression correlates with advanced disease in renal cancer," Cancer, vol. 10, 2010, 6 pages.
Wang, Bao-Ying et al., Hepatotoxicity and gene expression down-regulation of CYP isozymes caused by renal ischemia/reperfusion in the rat, Experimental and Toxicologic Pathology 61 (2009) 169-176.
Wong, Dona L. et al., "Adrenergic Responses to Stress: Transcriptional and Post-Transcriptional Changes," Ann N Y Acad Sci. Author manuscript; available in PMC, 2009, 10 pages.
Wu, Huiling et al., "TLR4 activation mediates kidney ischemia/reperfusion injury," The Journal of Clinical Investigation, vol. 117, No. 10, 2007, 2847-2859.
Xie, Chaoqin, "Ablation of Transient Receptor Potential Vanilloid 1 Abolishes Endothelin-Induced Increases in Afferent Renal Nerve Activity: Mechanisms and Functional Significance," Hypertension, vol. 54, 2009, 1298-1305.
Xie, Chaoqin, Interdependent Regulation of Afferent Renal Nerve Activity and Renal Function: Role of Transient Receptor Potential Vanilloid Type 1, Neurokinin 1, and Calcitonin Gene-Related Peptide Receptors, The Journal of Pharmacology and Experimental Therapeutics, vol. 325, No. 3, 7 pages.
Yoshino, Jun et al., "Leukemia Inhibitory Factor is Involved in Tubular Regeneration after Experimental Acute Renal Failure," J Am Soc Nephrol, vol. 14, 2003, 3090-3101.
Yuan, B. et al., "Gene expression reveals vulnerability to oxidative stress and interstitial fibrosis of renal outer medulla to nonhypertensive elevations of ANG II," Am J. Physiol Regul Integr Comp Physiol, vol. 284, 2003, 12 pages.
Zager, Richard et al., "Acute unilateral ischemic renal injury induces progressive renal inflammation, lipid accumulation, histone modification, and "end-stage" kidney disease," Am J Physiol Renal Physiol, vol. 301, 2011, 12 pages.

(56) References Cited

OTHER PUBLICATIONS

Zeisberg, Michael, "Bone morphogen protein-7 and the kidney: current; concepts and open questions," Nephrol Dial Transplant, vol. 21, 2006, 6 pages.

Zerega, Barbara et al., "Expression of NRL/NGAL (neu-related lipocalin/neutrophil gelatinase-associated lipocalin) during mammalian embryonic development and in Inflammation," European Journal of Cell Biology, vol. 79, 2000 8 pages.

Zhang, Weiru et al. "Interleukin 6 Underlies Angiotensin II-Induced Hypertension and Chronic Renal Damage," Hypertension, vol. 59, 2012, 136-144.

Zhao, Hongcheng et al., "Activatin of the Transcription Factor Oct-1 in Response to DNA Damage," Cancer Res, vol. 60, 2000, 6 pages.

Staal, S.S., et al., "A Prefilled, ; Ready-to-Use, Electrophoresis-Based ; Lab-on-a-Chip Device for Monitoring Ions in ; Blood and Urine." 14th International ; Conference on Miniaturized Systems for ; Chemistry and Life Sciences, Oct. 3-7, 2010, Groningen, The Netherlands. 3 pages.

Rusling, James F., "Nanomaterials-; Based Electrochemical Immunosensors; for Proteins," The Chemical Record, 12 (1), Feb. 2012. 13 pages.

Yanase, Yuhki, et al., "Development of an; Optical Fiber SPR Sensor for Living Cell; Activation." Biosensors and Bioelectronics, 25 (5), Jan. 15, 2010. 16 pages.

Chinushi et al., "Blood Pressure and Autonomic Responses to Electrical Stimulation of the Renal Arterial Nerves Before and After Ablation of the Renal Artery." Hypertension, 2013, 61, pp. 450-456.

Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.

International Search Report andWritten Opinion for International App. No. PCT/US2013/030041, dated Sep. 23, 2013, 20 pages.

Search Report dated Oct. 17, 2013 for European Application No. 13159256.

* cited by examiner

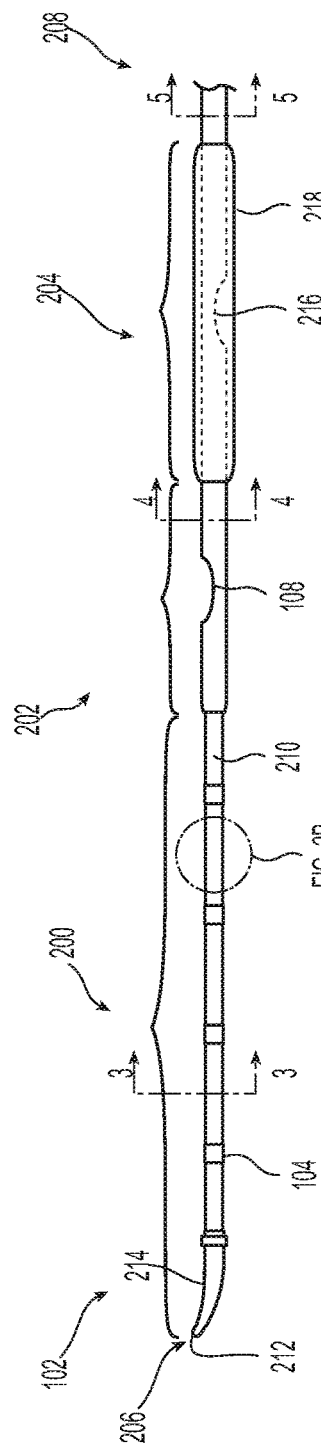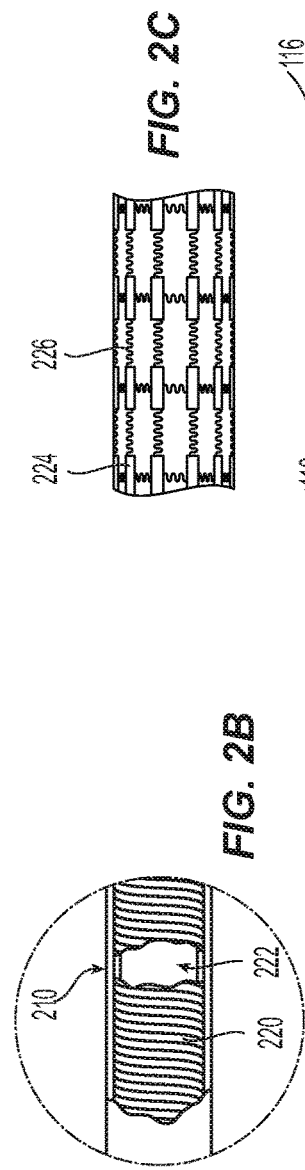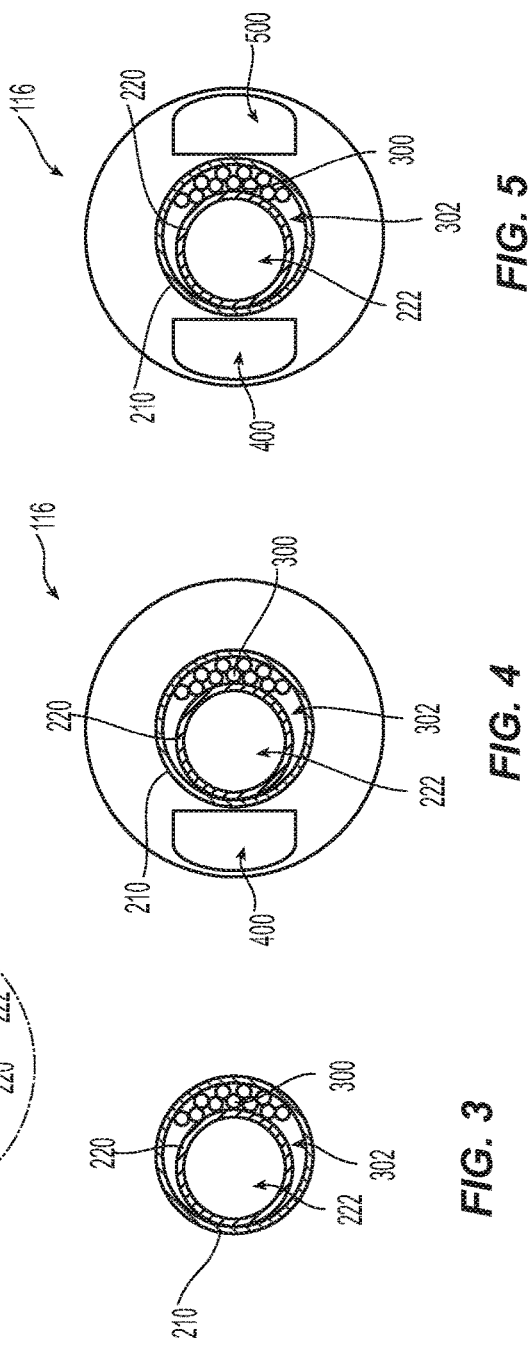

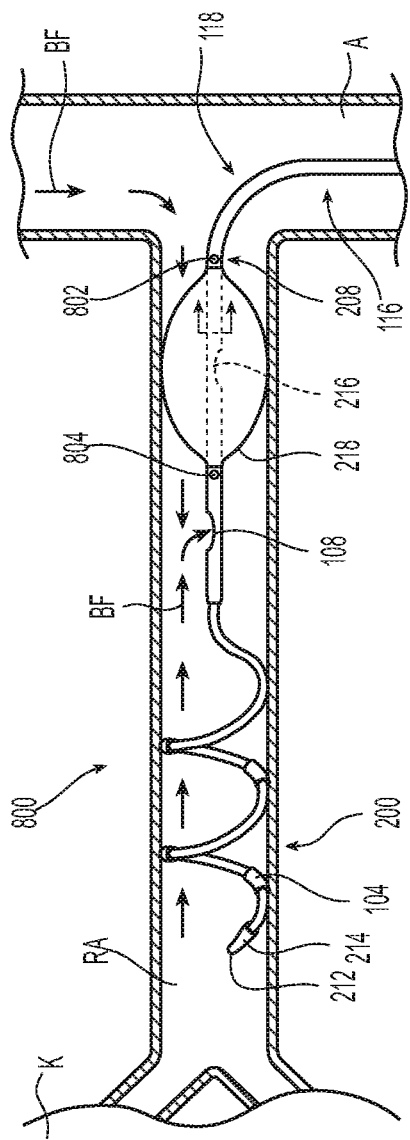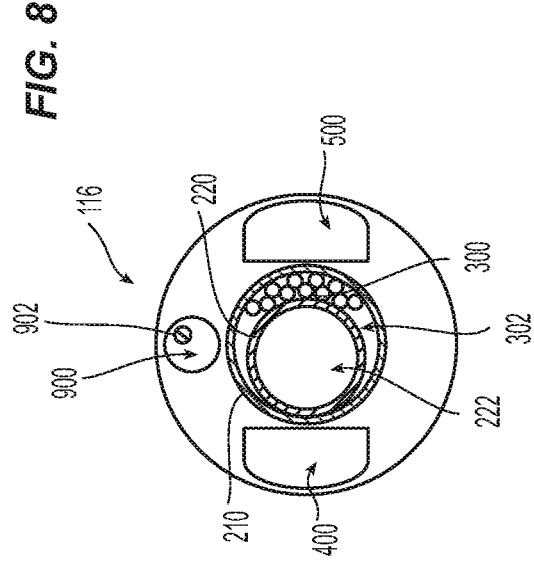
FIG. 8
FIG. 9

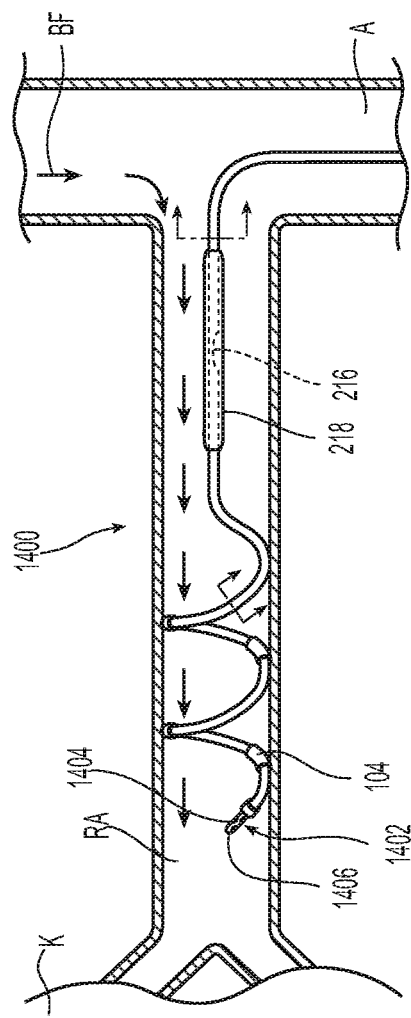
FIG. 14
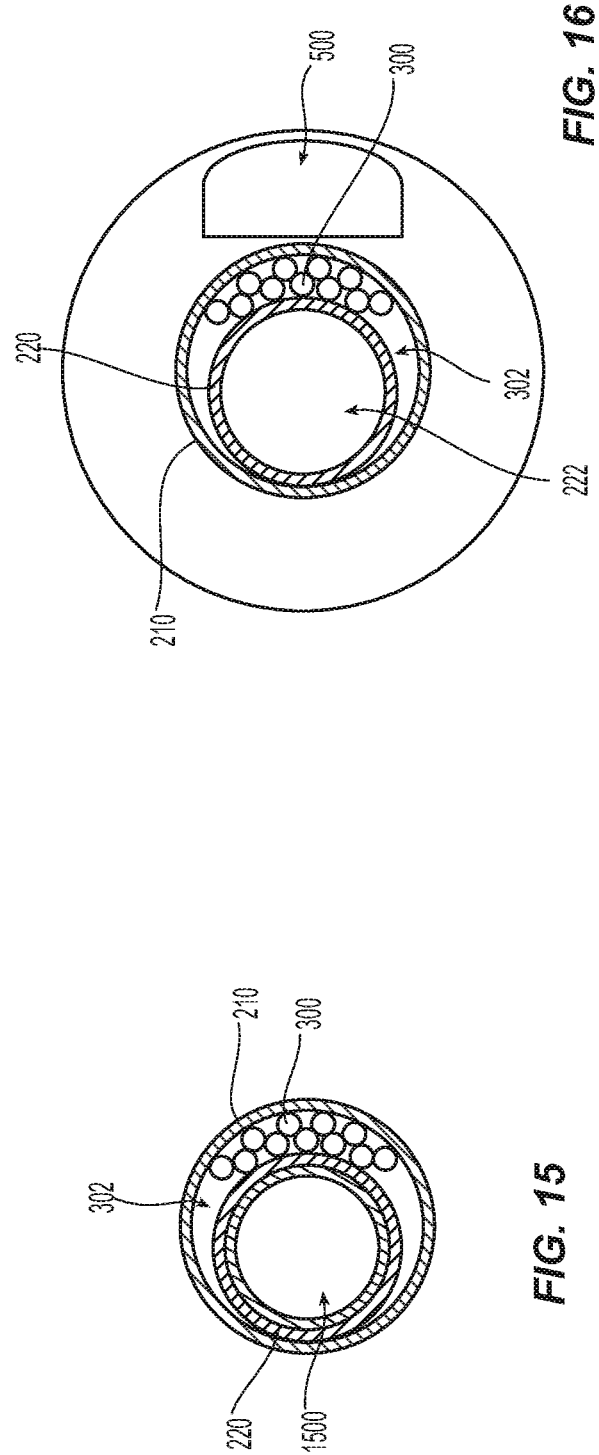
FIG. 16
FIG. 15

*Arterial Vasculature*

*Venous Vasculature*

BIOMARKER SAMPLING IN THE CONTEXT OF NEUROMODULATION DEVICES, SYSTEMS, AND METHODS

CROSS-REFERENCE TO RELATED APPLICATIONS

The present application is a divisional application of U.S. patent application Ser. No. 13/791,751, filed Mar. 8, 2013, now U.S. Pat. No. 9,597,018, which claims the benefit of the following applications:

(a) U.S. Provisional Application No. 61/608,625, filed Mar. 8, 2012;
(b) U.S. Provisional Application No. 61/608,626, filed Mar. 8, 2012; and
(c) U.S. Provisional Application No. 61/746,528, filed Dec. 27, 2012.

All of the foregoing applications are incorporated herein by reference in their entireties. Further, components and features of embodiments disclosed in the applications incorporated by reference may be combined with various components and features disclosed and claimed in the present application.

ADDITIONAL APPLICATION(S) INCORPORATED BY REFERENCE

The following application is also incorporated herein by reference in its entirety:

U.S. patent application Ser. No. 13/791,681, entitled "MONITORING OF NEUROMODULATION USING BIOMARKERS," filed Mar. 8, 2013.

As such, components and features of embodiments disclosed in this application may be combined with various components and features disclosed in the present application.

TECHNICAL FIELD

The present technology relates generally to biomarker sampling in the context of neuromodulation devices, systems, and methods. Some embodiments, for example, are directed to catheters, catheter systems, and methods for sampling biomarkers that change in response to neuromodulation.

BACKGROUND

The sympathetic nervous system (SNS) is a primarily involuntary bodily control system typically associated with stress responses. Fibers of the SNS innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate that result from renal sympathetic efferent stimulation are likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2A is an enlarged side view illustrating a neuromodulation and sampling assembly of the treatment device of FIG. 1 configured in accordance with an embodiment of the present technology.

FIG. 2B is a further enlarged cut-away view of a portion of the neuromodulation and sampling assembly of FIG. 2A in accordance with an embodiment of the present technology.

FIG. 2C is an enlarged top view of a portion of the occlusion member of FIG. 2A in accordance with another embodiment of the present technology.

FIGS. 3-5 are cross-sectional end views taken, respectively, along lines 2-2, 3-3 and 4-4 in FIG. 2A.

FIG. 8 is an enlarged side view illustrating the neuromodulation and sampling assembly of the treatment device of FIG. 1 having a perfusion lumen configured in accordance with an embodiment of the present technology.

FIG. 9 is a cross-sectional end view taken along line 9-9 in FIG. 8.

FIG. 14 is a cross-sectional view of a neuromodulation and sampling assembly in accordance with an embodiment of the present technology.

FIGS. 15-16 are cross-sectional end views taken, respectively, along lines 15-15 and 16-16 in FIG. 14.

DETAILED DESCRIPTION

Figure 1:
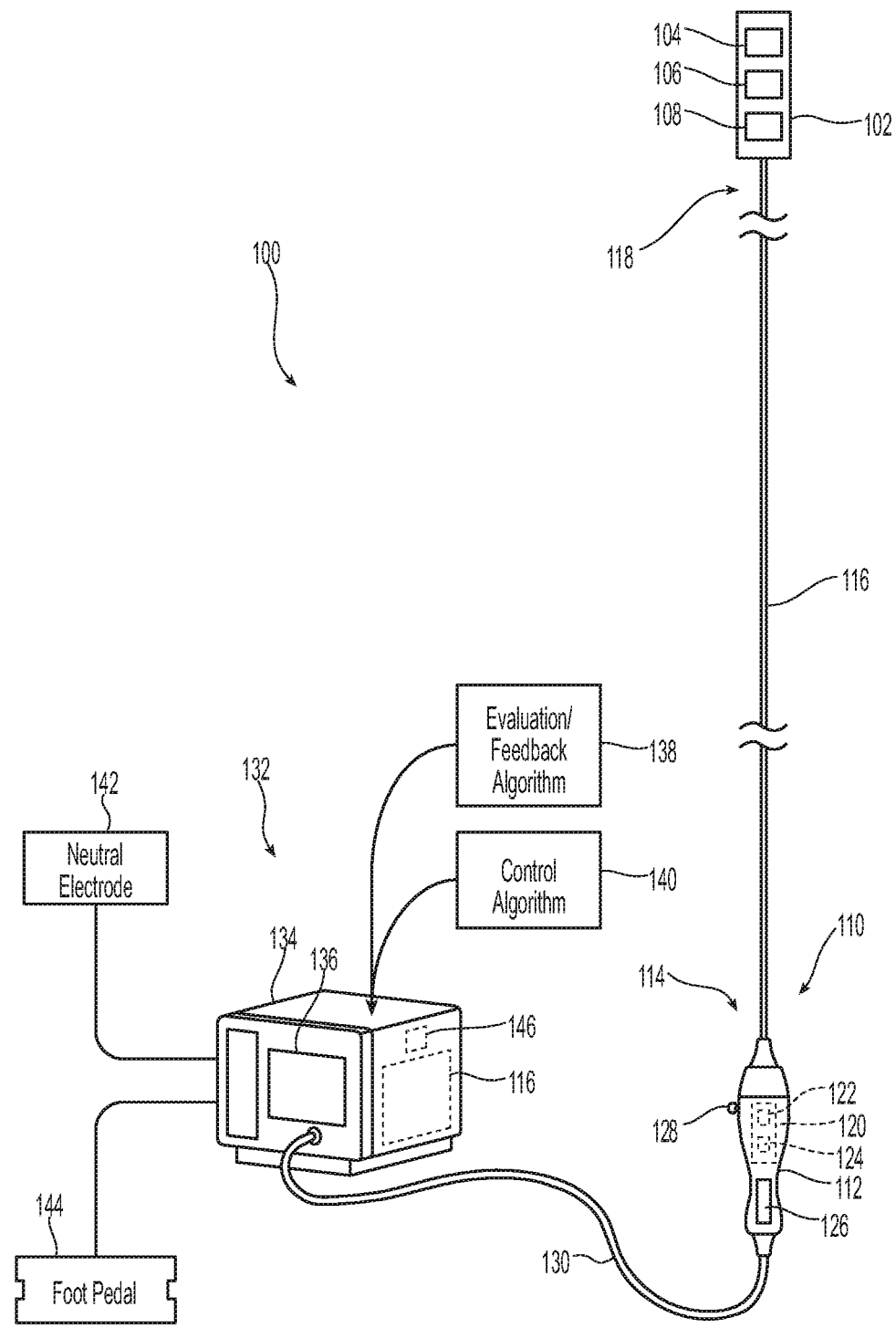
FIG. 1 is a partially-schematic perspective view illustrating a renal neuromodulation system including a treatment device configured in accordance with an embodiment of the present technology.

The present technology is directed to biomarker sampling in the context of neuromodulation devices, systems, and methods. Some embodiments, for example, are directed to catheters, catheter systems, and methods for sampling biomarkers that change in response to neuromodulation. Specific details of several embodiments of the technology are described below with reference to FIGS. 1-31B. Although many of the embodiments are described below with respect to systems, devices, and methods for endovascularly sampling biomarkers related to renal neuromodulation, other applications (e.g., sampling biomarkers also or alternatively related to neuromodulation of other peripheral nerves, treatments other than neuromodulation, effects, etc.) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-31B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Renal Neuromodulation

Renal neuromodulation is the partial or complete incapacitation or other effective disruption of nerves innervating the kidneys (e.g., rendering neural fibers inert or inactive or otherwise completely or partially reduced in function). For example, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures. Regardless of the type of heat exposure utilized to induce the thermal neuromodulation, a therapeutic effect (e.g., a reduction in renal sympathetic nerve activity (RSNA)) is expected.

Various techniques can be used to partially or completely incapacitate neural pathways, such as those innervating the kidneys. The purposeful application of energy (e.g., RF energy, mechanical energy, acoustic energy, electrical energy, thermal energy, etc.) to tissue and/or the purposeful removal of energy (e.g., thermal energy) from tissue can induce one or more desired thermal heating and/or cooling effects on localized regions of the tissue. The tissue, for example, can be tissue of the renal artery and adjacent regions of the renal plexus, which lay intimately within or adjacent to the adventitia of the renal artery. For example, the purposeful application and/or removal of energy can be used to achieve therapeutically effective neuromodulation along all or a portion of the renal plexus.

In the era of evidence-based medicine, evaluating the efficacy of a neuromodulation treatment can be important in gauging whether a treated patient may need additional neuromodulation treatment and/or alternative treatment. Many current neuromodulation systems assess neuromodulation efficacy by measuring and analyzing various physiological parameters (e.g., heart rate, blood pressure, etc.). However, statistically meaningful changes in such physiological parameters may not be observed until at least two weeks (and in most cases, months) after completion of the treatment. In the absence of real-time or at least relatively contemporaneous feedback, nerves that are under ablated, over ablated, or missed altogether may go undetected, or at the very least may not be clinically addressed until weeks or months after the initial treatment. Disclosed herein are several embodiments of devices, systems, and methods that facilitate relatively rapid analysis of neuromodulation efficacy by detecting changes in the level and/or activity of one or more target biomarkers associated with neuromodulation.

II. Selected Embodiments of Neuromodulation Systems

FIG. 1 is a partially-schematic diagram illustrating a system 100 configured in accordance with an embodiment of the present technology. The system 100 can include a treatment device 110 (e.g., a catheter) operably coupled to a console (e.g., an energy generator) 132 via a connector 130 (e.g., a cable). As shown in FIG. 1, the treatment device 110 can include an elongated shaft 116 having a proximal portion 114, a handle assembly 112 at a proximal region of the proximal portion 114, and a distal portion 118 extending distally relative to the proximal portion 114. The elongated shaft 116 can be configured to locate the distal portion 118 intravascularly (e.g., within a renal artery) or within another suitable body lumen (e.g., within a ureter) at a treatment location. The treatment device 110 can further include a neuromodulation and sampling assembly 102 carried by or affixed to the distal portion 118 of the elongated shaft 116. The neuromodulation and sampling assembly 102 can include one or more energy delivery elements 104 (shown schematically in FIG. 1) (e.g., electrodes) configured to modulate nerves at or near the treatment location as well as one or more sampling ports 108 (also shown schematically in FIG. 1) configured to collect biological samples from the treatment location or another suitable location near the treatment location. As used herein, a "biological sample" or "sample" may refer to any suitable bodily fluid (e.g., blood, plasma, urine, etc.) or tissue that may be affected by neuromodulation (e.g., that may contain one or more target biomarkers affected by neuromodulation).

The system 100 can further include an analyzer 120 (e.g., a biosensor) configured to receive and analyze the biological sample collected by the neuromodulation and sampling assembly 102. This analysis, for example, can detect a change in a biological parameter related to neuromodulation (e.g., the level or activity of one or more target biomarkers within the sample). As used herein, a "target biomarker" may be any biomolecule that exhibits a quantitative and/or detectable change in level or activity following neuromodulation. In some embodiments, changes in the level or activity of a target biomarker may be a direct result of neuromodulation (e.g., a direct response to neuronal damage). For example, sympathetic neuromodulation may result in the discharge of neurotransmitter reserves from synaptic ends of nerves at or near the kidney, resulting in a biomarker concentration increase (e.g., a biomarker concentration burst or spike) that can be detected within a collected biological fluid (e.g., renal arterial blood, renal venous blood, systemic blood, or urine, among others). In addition or alternatively, changes in the level or activity of a target biomarker may be an indirect and/or surrogate response to neuromodulation. For example, a target biomarker may be a protein such as an inflammatory or anti-inflammatory pathway protein, a heat shock response pathway protein, or a stress response pathway protein that exhibits a change in level or activity in response to exposure to neuromodulating energy (e.g., RF energy), a change in temperature at or near a treatment site, or another change accompanying a neuromodulation treatment.

Examples of non-protein target biomarkers include catecholamines and other neurotransmitters (e.g., those associated with sympathetic nervous activity, such as norepinephrine ("NE")), neuropeptide Y ("NPY"), epinephrine, dopamine, secreted hormonal and other soluble endocrine molecules, and secreted metabolites and cellular debris, among others. Examples of protein target biomarkers include cell surface proteins, secreted proteins, and intracellular proteins, among others. Other examples of target biomarkers and detection methods may be found in U.S. Provisional Application No. 61/608,625, filed Mar. 8, 2012, and U.S. Provisional Application No. 61/746,528, filed Dec. 27, 2012. As noted previously, both of these application are incorporated herein by reference in their entireties.

As shown in FIG. 1, the analyzer 120 can be incorporated into the handle 112 of the treatment device 110 and can be configured to receive a collected biological sample via the elongated shaft 116. The analyzer 120 can include one or more detection agents (e.g., a substrate for a target biomarker or an enzyme or catalytic antibody for which the target biomarker is a substrate) and/or capture agents (e.g., an agent that specifically binds to a target biomarker and/or binds to an enzymatic product or by-product of the target biomarker), a physicochemical transducer 122 (e.g., an optical transducer, a piezoelectric transducer, an electrochemical transducer, etc.), and a processing device 124 having processing circuitry (e.g., a microprocessor).

Upon receipt of the sample by the analyzer 120, detection and/or capture agents within the analyzer 120 can interact with target biomarkers of the collected sample, if present. In at least some cases, binding of a target biomarker to a capture agent and/or interaction of the target biomarker with a detection agent can result in a biomarker response (e.g., a change in color, formation of a reaction product, or another suitable response). The physicochemical transducer 122 can transform the biomarker response into a more easily measureable and quantifiable signal (e.g., a colorimetric, fluorescent, heat, energy, or electric signal) that can be sensed by or communicated to the processing device 124 for storage and/or analysis. The processing device 124 can be operably coupled to an indicator 126 carried by the handle 112. The indicator 126 can be configured to indicate suitable information related to processing the target biomarker (e.g., a sample date, a status of the target biomarker, and/or a status of nerve modulation based on a detected level or activity of the target biomarker). The indication can be auditory and/or visual. In some embodiments, the indicator 126 includes a suitable display component, such as a light emitting diode, an imaging display, and/or a graphical user interface.

In some embodiments, the analyzer 120 is integrated into the console 132 instead of the handle 112. In these embodiments, for example, the analyzer 120 can be configured to receive a biological sample directly from the treatment device 110 (e.g., via a fluid conduit (not shown) (e.g., polymer tubing) within or separate from the connector 130). The fluid conduit can extend between the treatment device 110 and the console 132 where an air or fluid pump (not shown) integrated with the analyzer 120 can draw a biological sample into a portion of the analyzer 120. Alternatively, the air or fluid pump can be housed in the handle 112 to transfer a biological sample to the analyzer 120 contained within the console. In these and other embodiments, the handle 112 can include a removable container (not shown) configured to receive a biological sample collected via the sampling port 108 and conveyed to the container via the shaft 116. For detection and/or analysis of a target biomarker within the sample, the removable container can be removed from the handle 112 and transferred to the analyzer 120 (e.g., when the analyzer 120 is a remote a standalone device or when the analyzer 120 integrated into the console 132, and/or in other embodiments in which the analyzer 120 is remote relative to the treatment device 110). The removable container may be reusable or disposable.

The console 132 can be configured to generate a selected form and/or magnitude of energy for delivery to the treatment site via the energy delivery element 104 of the neuromodulation and sampling assembly 102. For example, the console 132 can include an energy generator (not shown) configured to generate RF energy (monopolar or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, chemicals (e.g., drugs or other agents), radiation (e.g., infrared, visible, gamma), or another suitable type of energy. In some embodiments, neuromodulation may be achieved by chemical-based treatment including delivering one or more chemicals (e.g., guanethidine, ethanol, phenol, a neurotoxin (e.g., vincristine)), or another suitable agent selected to alter, damage, or disrupt nerves. In a particular embodiment, the console 132 includes a RF generator operably coupled to one or more energy delivery elements 104 of the neuromodulation and sampling assembly 102. Furthermore, the console 132 can be configured to control, monitor, supply, or otherwise support operation of the treatment device 110. For example, a control mechanism, such as foot pedal 144, may be connected (e.g., pneumatically connected or electrically connected) to the console 132 to allow an operator to initiate, terminate and/or adjust various operational characteristics of the energy generator, such as power delivery. In some embodiments, the console 132 may be configured to provide delivery of a monopolar electric field via the energy delivery element 104. In such embodiments, a neutral or dispersive electrode 142 may be electrically connected to the console 132 and attached to the exterior of the patient (not shown).

In some embodiments, the system 100 includes a remote control device (not shown) that can be configured to be sterilized to facilitate its use within a sterile field. The remote control device can be configured to control operation of the neuromodulation and sampling assembly 102, the console 132, and/or other suitable components of the system 100. For example, the remote control device can be configured to allow for selective activation of the neuromodulation and sampling assembly 102. In other embodiments, the remote control device may be omitted and its functionality may be incorporated into the handle 112 or console 132.

As shown in FIG. 1, the console 132 can include a primary housing 134 having a display 136. In some embodiments, the console 132 includes a controller 146 having processing circuitry (e.g., a microprocessor). The console 132 can be configured to execute an automated control algorithm 140 and/or to receive control instructions from an operator. Furthermore, the console 132 can be configured to provide feedback to an operator before, during, and/or after a treatment procedure via the display 136 and/or via an evaluation/feedback algorithm 138. For example, the feedback can be based on output from the analyzer 120. The controller 146 can be configured to execute stored instructions relating to the control algorithm 140 and/or the evaluation/feedback algorithm 138.

The console 132 can be configured to communicate with the treatment device 110 (e.g., via the connector 130). For example, the neuromodulation and sampling assembly 102 and/or the shaft 116 can include a sensor 106 (e.g., a chemical sensor, a temperature sensor, a pressure sensor, or a flow rate sensor) and a sensor lead (not shown) (e.g., an electrical lead or a pressure lead) configured to carry a signal from the sensor 106 to the handle 112. The connector 130 can be configured to carry the signal from the handle 112 to the console 132. The controller 146 of the console 132 can be configured to communicate with the processing device 124 of the analyzer 120 (e.g., via the connector 130, Bluetooth, wireless, or in another suitable manner when the analyzer 120 is within the handle 112 or otherwise remote relative to the console 132).

In some embodiments, the console 132 includes a vacuum 148 or other suitable negative pressure source (e.g., a syringe) operably coupled to the sampling port 108 of the neuromodulation and sampling assembly 102. In other embodiments, the vacuum 148 can be a standalone device separate from the console 132. The vacuum 148 can be in fluid connection with the sampling port 108 via the shaft 116. Negative pressure generated by the vacuum 148 can be used, for example, to draw a biological sample into the sampling port 108. In yet other embodiments, the treatment device 110 can include an adapter (not shown) (e.g., a luer lock) configured to be operably coupled to a syringe (not shown) and the syringe can be used to apply negative pressure to the shaft 116.

FIG. 2A is a side view illustrating the neuromodulation and sampling assembly 102 in a low-profile or delivery state in accordance with an embodiment of the present technology. The neuromodulation and sampling assembly 102 can include a neuromodulation element 200, a sampling element 202, and an occlusion element 204. In some embodiments, the neuromodulation element 200 and the sampling element 202 are distal to the occlusion element 204 and the neuromodulation element 200 is distal to the sampling element 202. In other embodiments, the neuromodulation element 200 and the sampling element 202 are distal to the occlusion element 204 and the sampling element 202 is distal to the neuromodulation element 200. In still other embodiments, the neuromodulation element 200, the sampling element 202, and the occlusion element 204 can have another suitable arrangement. A proximal region 208 of the neuromodulation and sampling assembly 102 can be carried by or affixed to the distal portion 118 of the elongated shaft 116. For example, all or a portion (e.g., a proximal portion) of the neuromodulation and sampling assembly 102 can be an integral extension of the shaft 116. In some embodiments, the profile of the neuromodulation and sampling assembly can increase between the neuromodulation element 200 and the sampling element 202. A distal region 206 of the neuromodulation and sampling assembly 102 may terminate distally with, for example, an atraumatic, flexible curved tip 214 having an opening 212 at its distal end. In some embodiments, the distal region 206 of the neuromodulation and sampling assembly 102 may also be configured to engage another element of the system 100 or treatment device 110.

FIG. 2B is an enlarged view of a portion of the neuromodulation and sampling assembly 102 of FIG. 2A. FIG. 3 is a cross-sectional end view taken along line 3-3 in FIG. 2A. Referring to FIGS. 2A-3 together, the neuromodulation and sampling assembly 102 can include the one or more energy delivery elements 104 (e.g., RF electrodes, ultrasound transducers, cryotherapeutic cooling assemblies, etc.) carried by a support structure 210 as part of the neuromodulation element 200. The energy delivery elements 104, for example, can be separate band electrodes axially spaced apart along the support structure 210 (e.g., adhesively bonded to the support structure 210 at different positions along the length of the support structure 210). In other embodiments, the neuromodulation and sampling assembly 102 may have a single energy delivery element 104 at or near the distal portion 118 of the shaft 116.

In some embodiments, the energy delivery elements 104 are formed from a suitable electrically conductive material (e.g., a metal, such as gold, platinum, alloys of platinum and iridium, etc.). The number, arrangement, shape (e.g., spiral and/or coil electrodes) and/or composition of the energy delivery elements 104 may vary. The individual energy delivery elements 104 can be electrically connected to the console 132 by a conductor or bifilar wire 300 extending through a lumen 302 of the shaft 116 and/or support structure 210. For example, the individual energy delivery elements 104 may be welded or otherwise electrically coupled to corresponding energy supply wires 300, and the wires 300 can extend through the elongated shaft 116 for the entire length of the shaft 116 such that proximal ends of the wires 300 are coupled to the handle 112 and/or to the console 132.

As shown in the enlarged cut-away view of FIG. 2B, the support structure 210 can be a tube (e.g., a flexible tube) and the neuromodulation and sampling assembly 102 can include a pre-shaped control member 220 positioned within the tube. Upon deployment, the control member 220 can bias at least a portion of the neuromodulation and sampling assembly 102 (e.g., the neuromodulation element 200) into a deployed state (FIG. 6C or 6D). For example, the control member 220 can have a pre-set configuration that gives at least a portion of the neuromodulation and sampling assembly 102 a helical or spiral configuration in the deployed state (FIG. 6C or 6D). In some embodiments, the control member 220 includes a tubular structure comprising a nitinol multifilar stranded wire with a lumen 222 therethrough and sold under the trademark HELICAL HOLLOW STRAND (HHS), and commercially available from Fort Wayne Metals of Fort Wayne, Ind. The lumen 222 can define a passageway for receiving a guide wire 600 that extends proximally from the opening 212 at the tip 214 of the neuromodulation and sampling assembly 102. In other embodiments, the control member 220 may be composed of different materials and/or have a different configuration. For example, the control member 220 may be formed from other suitable shape memory materials (e.g., nickel-titanium (nitinol), shape memory polymers, electro-active polymers) that are pre-formed or pre-shaped into the desired deployed state. Alternatively, the control member 220 may be formed from multiple materials such as a composite of one or more polymers and metals.

Referring to FIG. 3 (a cross-sectional end view taken along line 3-3 in FIG. 2A), the support structure 210 can be configured to fit tightly against the control member 220 and/or wires 300 to reduce space between an inner portion of the support structure 210 and the components positioned therein. For example, the control member 220 and the inner wall of the support structure 210 can be in intimate contact such that there is little or no space between the control member 220 and the support structure 210. Such an arrangement can help to reduce or prevent the formation of wrinkles in the neuromodulation and sampling assembly 102 during deployment. The support structure 210 may be composed of a polymer material such as polyamide, polyimide, polyether block amide copolymer sold under the trademark PEBAX, polyethylene terephthalate (PET), polypropylene, aliphatic, polycarbonate-based thermoplastic polyurethane sold under the trademark CARBOTHANE, a polyether ether ketone (PEEK) polymer, or another suitable material that provides sufficient flexibility to the support structure 210.

The curved tip 214 can be configured to provide an exit (e.g., via the opening 212) for a guide wire that directs the guide wire away from a wall of a vessel or lumen at or near a treatment location. As a result, the curved tip 214 can facilitate alignment of the neuromodulation and sampling assembly 102 in the vessel or lumen as it expands from the delivery state shown in FIG. 2A. Furthermore, the curved tip 214 can reduce the risk of injuring a wall of a vessel or lumen when the distal end of the guide wire is advanced from the opening 212. The curvature of the tip 214 can be varied depending upon the particular sizing/configuration of the neuromodulation and sampling assembly 102 and/or anatomy at a treatment location. In some embodiments, the tip 214 may also comprise a radiopaque marker and/or one or more sensors (not shown). The tip 214 can be affixed to the distal end of the support structure 210 via adhesive, crimping, over-molding, or other suitable techniques.

The flexible curved tip 214 can be made from a polymer material (e.g., polyether block amide copolymer sold under the trademark PEBAX), a thermoplastic polyether urethane material (sold under the trademarks ELASTHANE or PELLETHANE), or other suitable materials having the desired properties, including a selected durometer. As noted above, the tip 214 is configured to provide an opening for the guide wire, and it is desirable that the tip itself maintain a desired shape/configuration during operation. Accordingly, in some embodiments, one or more additional materials may be added to the tip material to help improve tip shape retention. In one particular embodiment, for example, about 5 to 30 weight percent of siloxane can be blended with the tip material (e.g., the thermoplastic polyether urethane material), and electron beam or gamma irradiation may be used to induce cross-linking of the materials. In other embodiments, the tip 214 may be formed from different material(s) and/or have a different arrangement.

FIGS. 4 and 5 are cross-sectional end views taken, respectively, along lines 4-4 and 5-5 of FIG. 2A. With reference to FIGS. 2A-5 together, the neuromodulation and sampling assembly 102 can include the sampling port 108 as part of the sampling element 202. The sampling port 108 can be in fluid connection with a sampling lumen 400 that extends proximally along the shaft 116 from sampling port 108 to the handle 112. In some embodiments, the sampling lumen 400 can be coupled to the vacuum 148 or a syringe (not shown) to facilitate retrieval of a sample through the sampling port 108 and conveyance of the sample along the sampling lumen 400. To prevent the sample from contaminating the vacuum 148 or syringe, the sampling lumen 400 can include a one-way valve or seal (not shown) at a location along the length of the sampling lumen 400 distal to the negative pressure source inlet. In some embodiments, an inner cross-sectional area of the sampling lumen 400 and/or an area of the sampling port can be selected to achieve an adequate pressure drop across the sampling port 108.

The sampling element 202 can further include an occlusion member 218 (e.g., a compliant, semi-compliant, or non-compliant balloon, an expandable basket, a stent-like structure, etc.) as part of the occlusion element 204. The occlusion member 218 can be configured to at least partially occlude a vessel (e.g., a renal artery) or lumen in which the neuromodulation and sampling assembly 102 is positioned. In some embodiments, the occlusion member 218 extends around a segment of the shaft 116 that includes an inflation opening 216. For example, the occlusion member 218 can be laser-bonded or adhered by other suitable methods to an outer surface of the shaft 116 at axially spaced apart locations distal and proximal, respectively, relative to the inflation opening 216.

The inflation opening 216 can connect to an inflation lumen 500 that extends proximally along the shaft 116 from the inflation opening 216 to the handle 112. Control of the occlusion element 204 and/or occlusion member 218 (e.g., control over inflation/expansion volume, inflation/expansion timing and/or deflation/collapse timing) can be manual or automatic (e.g., based on a pre-set schedule or algorithm). Based on a desired level of occlusion (e.g., full, partial, etc.) and/or perfusion (e.g., none, controlled, etc.) and an input value corresponding to a size of a vessel or lumen (e.g., as measured from pre-operative fluoroscopic images), or another suitable parameter or group of parameters (e.g., pressure, flow rates, temperature, etc.), the occlusion member 218 can be expanded (e.g., automatically expanded) to a specific, desired expanded volume and/or outer diameter. In some embodiments, the occlusion member 218 is inflated and/or expanded to a level selected to cause partial occlusion of a vessel or lumen. Partial rather than complete occlusion can be useful, for example, to reduce or prevent ischemia, to facilitate replenishment of a biological fluid after sampling, and/or for other reasons.

In some embodiments, one or more pressure sensors 224 (e.g., micro-flow controllers, serially synchronized pressure sensors, pressure tubes, etc.) may be provided so that the occlusion member 218 automatically expands to an appropriate expanded volume without the need to input a vessel or lumen size prior to inflation. For example, as shown in the enlarged top view of the occlusion member 218 in FIG. 2C, the occlusion member 218 may be fully or partially fitted with one or more pressure sensors 224 that are interconnected by one or more stretchy, serpentine-shaped wires 226 configured to buckle and/or adapt as the occlusion member 218 expands/inflates and/or collapses. The pressure sensors 224 can be electrically coupled to the handle 112 and/or that console 132 by one or more wires (not shown) extending through the shaft. The console 132 may include one or more customizable algorithms that detect an increase and/or decrease in pressure exerted on the pressure sensors 224 by the interconnecting wires 226 (e.g., as the occlusion member 218 expands/inflates and/or collapses) to control inflation and/or expansion of the occlusion member 218. Furthermore, in some embodiments, the occlusion member 218 can be formed in an asymmetrical shape such that the vessel or lumen is not totally occluded when the occlusion member 218 is fully inflated and/or expanded so as to allow for perfusion.

As shown in FIG. 5, the sampling lumen 400 and the inflation lumen 500 can be positioned within the shaft 116 at least proximate to opposite sides of the lumen 222. In other embodiments, the sampling lumen 400 and the inflation lumen 500 can be positioned within the support structure 210. In yet other embodiments, the sampling lumen 400, the inflation lumen 500 and the lumen 222 can have other suitable shapes, sizes and/or arrangements.

Several embodiments of methods for utilizing the system 100 to provide real-time or relatively contemporaneous (e.g., less than 30 minutes) renal neuromodulation efficacy feedback in accordance with the present technology are described herein. In a particular embodiment, a method includes: (a) collecting a pre-neuromodulation biological sample at a treatment site via a sampling element 202 of a neuromodulation and sampling assembly 102; (b) determining a baseline or pre-neuromodulation level or activity of one or more target biomarkers within the pre-neuromodulation biological sample; (c) performing a neuromodulation procedure using a neuromodulation element 200 of the neuromodulation and sampling assembly 102; (d) expanding an occlusion member 218 to at least partially occlude a vessel or lumen in which the treatment site is located; (e) collecting a post-neuromodulation biological sample at the treatment site via the sampling element 202; (f) determining a post-neuromodulation level or activity for the target biomarker(s); and (g) comparing the post-neuromodulation level or activity to the baseline level or activity to provide neuromodulation efficacy feedback.

Figure 6A:
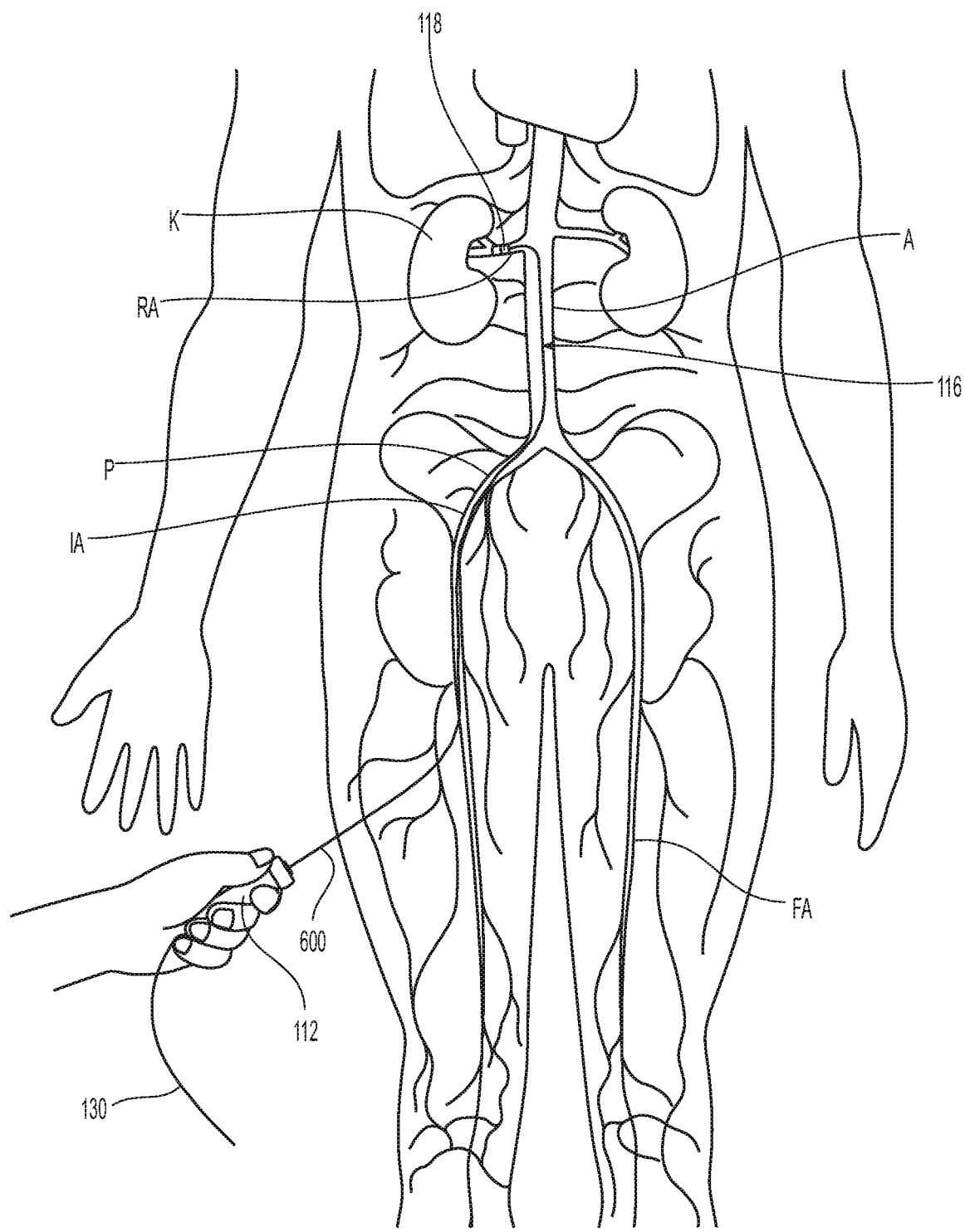
FIG. 6A is a partially cross-sectional anatomical front view illustrating advancing the treatment device shown in FIG. 1 along an intravascular path in accordance with an embodiment of the present technology.
Figure 6B:
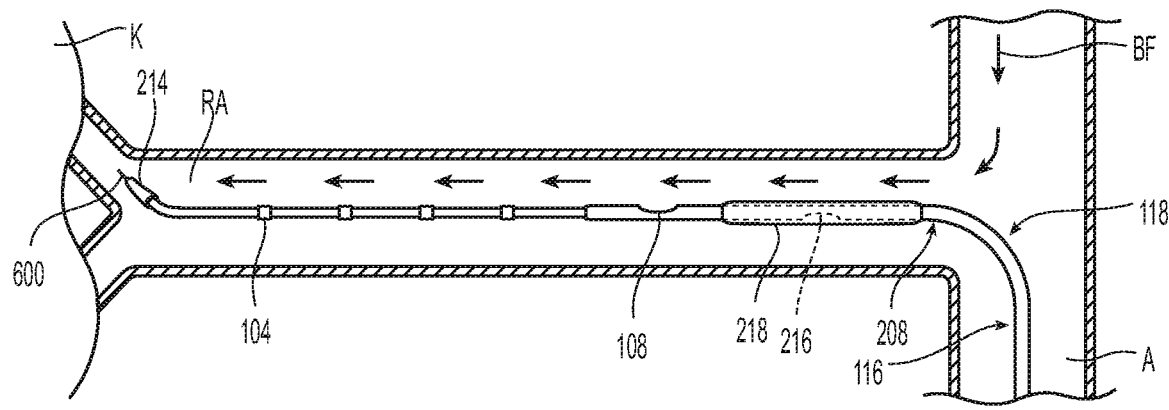
FIG. 6B is a cross-sectional view of the neuromodulation and sampling assembly shown in FIG. 2A within a renal artery in accordance with an embodiment of the present technology.
Figure 6C:
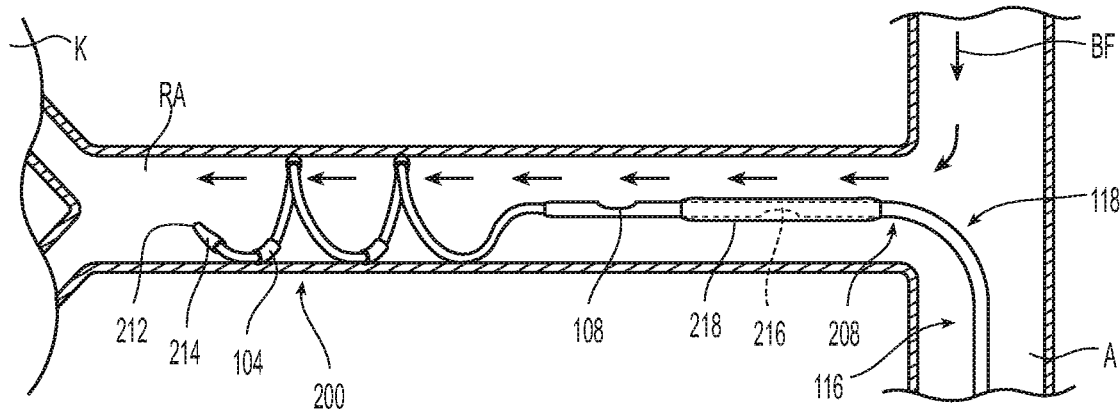
FIG. 6C is a cross-sectional view of the neuromodulation and sampling assembly shown in FIG. 2A illustrating deploying a portion of the neuromodulation and sampling assembly at a treatment location within the renal artery in accordance with an embodiment of the present technology.
Figure 6D:
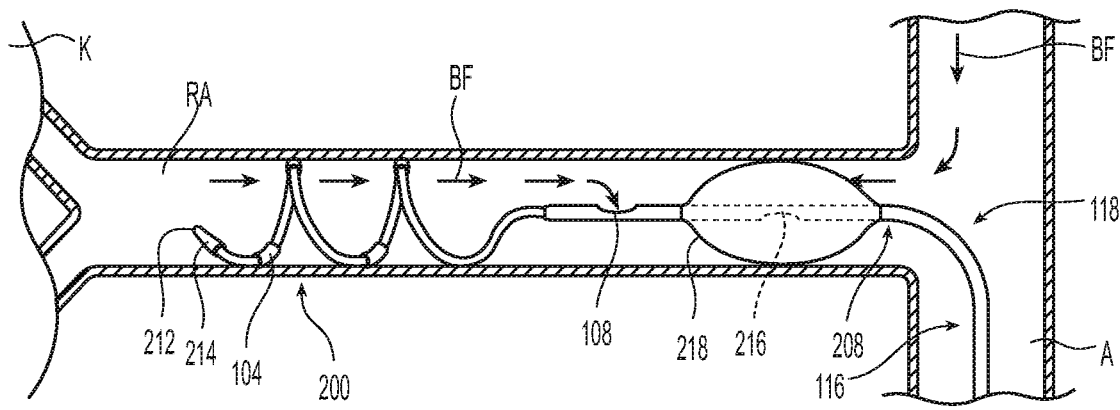
FIG. 6D is a cross-sectional view of the neuromodulation and sampling assembly of FIG. 2A illustrating occluding a portion of the renal artery at a treatment location in accordance with an embodiment of the present technology.

Referring to FIG. 6A, intravascular delivery of the neuromodulation and sampling assembly 102 can include percutaneously inserting a guide wire 600 within the vasculature at an access site (e.g., femoral, brachial, radial, or axillary artery) and moving the shaft 116 and the neuromodulation and sampling assembly 102 (in the delivery state) along the guide wire until at least a portion of the neuromodulation and sampling assembly 102 reaches the treatment location (as shown in FIG. 6B). In some embodiments, the shaft 116 and the neuromodulation and sampling assembly 102 can include the lumen 222 (FIGS. 3-5) configured to receive a guide wire 600 in an over-the-wire or rapid exchange configuration. As illustrated, a section of the proximal portion 114 of the shaft 116 can be extracorporeally positioned and manipulated by the operator (e.g., via the actuator 128) to advance the shaft 116 through the sometimes tortuous intravascular path (P) and remotely manipulate the distal portion 118 of the shaft 116.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation and sampling assembly 102. For example, a fluoroscopy system (e.g., including a flat-panel detector, x-ray, or c-arm) can be rotated to accurately visualize and identify the target treatment site. In other embodiments, the treatment site can be located using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the treatment device 110. Further, in some embodiments, image guidance components (e.g., IVUS, OCT) may be integrated with the treatment device 110 and/or run in parallel with the treatment device 110 to provide image guidance during positioning of the neuromodulation and sampling assembly 102. For example, image guidance components (e.g., IVUS or OCT) can be coupled to a distal portion of the treatment device 110 to provide three-dimensional images of the vasculature proximate the target site to facilitate positioning or deploying the neuromodulation and sampling assembly 102 within the target renal blood vessel.

Once the neuromodulation and sampling assembly 102 is positioned at a treatment location, the guide wire 600 can be at least partially introduced (e.g., inserted) into or removed (e.g., withdrawn) from the neuromodulation and sampling assembly 102 to transform or otherwise move the neuromodulation and sampling assembly 102 to a deployed state. In the deployed state, for example, the energy delivery elements 104 of the neuromodulation and sampling assembly 102 can be positioned in stable contact with a wall of the vessel or lumen for delivering energy, as illustrated by FIG. 6C. Though the embodiment shown in FIG. 6C shows a deployed neuromodulation and sampling assembly 102 in which only the neuromodulation element 200 is spiral or helically-shaped, in other embodiments, all or a greater portion of the neuromodulation and sampling assembly 102 can be spiral or helically-shaped. Furthermore, the neuromodulation element 200, the sampling element 202, and/or other portions of the neuromodulation and sampling assembly 102 can have other suitable shapes, sizes, and/or configurations (e.g., bent, deflected, helical, spiral, zig-zag, Malecot, etc.).

In some embodiments, the neuromodulation and sampling assembly 102 may be delivered to a treatment site within a guide sheath (not shown) with or without using the guidewire 600. When the neuromodulation and sampling assembly 102 is at the target site, the guide sheath may be at least partially withdrawn or retracted and the neuromodulation and sampling assembly 102 can be transformed into the deployed state. For example, at least a portion of the neuromodulation and sampling assembly 102 can have a shape memory corresponding to a deployed state and the sheath can prevent the neuromodulation and sampling assembly 102 from deploying in response to the shape memory before reaching the treatment location. In still other embodiments, the shaft 116 may be steerable itself such that the neuromodulation and sampling assembly 102 may be delivered to the treatment site without the aid of the guide wire 600 and/or guide sheath.

Examples of other suitable neuromodulation delivery configurations, deployment configurations and/or deployment mechanisms can be found in U.S. application Ser. No. 12/910,631, filed Oct. 22, 2010, entitled "APPARATUS, SYSTEMS, AND METHODS FOR ACHIEVING INTRAVASCULAR, THERMALLY-INDUCED RENAL NEUROMODULATION," U.S. application Ser. No. 13/281,361, filed Oct. 25, 2011, entitled "CATHETER APPARATUSES HAVING MULTI-ELECTRODE ARRAYS FOR RENAL NEUROMODULATION AND ASSOCIATED SYSTEMS AND METHODS," and U.S. Provisional Application No. 61/646,218, filed May 5, 2012, entitled "MULTI-ELECTRODE CATHETER ASSEMBLIES FOR RENAL NEUROMODULATION AND ASSOCIATED SYSTEMS AND METHODS," which are all incorporated herein by reference in their entireties.

In the deployed state, at least a portion of the neuromodulation and sampling assembly 102 can be configured to contact an inner wall of the renal artery and to cause a fully-circumferential lesion without the need for repositioning. For example, the neuromodulation element 200 can be configured to form a lesion or series of lesions (e.g., a helical/spiral lesion or a discontinuous lesion) that is fully-circumferential overall, but generally non-circumferential at longitudinal segments of the treatment location. This can facilitate precise and efficient treatment with a low possibility of vessel stenosis. In other embodiments, the neuromodulation element 200 can be configured to form a partially-circumferential lesion or a fully-circumferential lesion at a single longitudinal segment of the treatment location. In some embodiments, the therapeutic element 502 can be configured to cause therapeutically-effective neuromodulation (e.g., using ultrasound energy) without contacting a vessel wall.

At one or more timepoints prior to neuromodulation, the sampling element 202 of the assembly 102 can collect a pre-neuromodulation biological sample at or near the treatment site to determine an initial, pre-neuromodulation level or activity of one or more target biomarkers. In some embodiments, the collected baseline sample can be conveyed directly from the sampling port 108 through the sampling lumen 400 to the analyzer 120 (e.g., when the analyzer 120 is incorporated into the handle 112). The analyzer 120 can be configured to analyze the pre-neuromodulation sample to detect a baseline level of one or more target biomarkers. In other embodiments, the collected baseline sample can be conveyed directly from the sampling port 108 through the sampling lumen 400 to the console 132 via the connector 130 and/or a separate collection connector (not shown) between the handle 112 and the console 132. As discussed below, the baseline level or value can be compared to a post-neuromodulation level to evaluate the efficacy of the neuromodulation. When the analysis is complete, the baseline data obtained by the analyzer 120 from the baseline analysis may be stored by memory of the analyzer 120, or in some embodiments, the baseline data can be communicated (e.g., via the connector 130 and/or wirelessly) to memory of the console 132 for storage and/or processing. In addition, the baseline data may be displayed by an analyzer display (not shown) on the handle 112 and/or the console display 136 (FIG. 1). After the baseline data has been obtained, the baseline sample can be removed from the analyzer 120 in the handle 112 to prevent contamination of incoming samples. Furthermore, in some embodiments, the analyzer 120 can be configured to separate and store more than one sample (e.g., reducing or eliminating the need to service the analyzer 120 in between collections).

The baseline value may represent a target biomarker level or activity at a specific timepoint before neuromodulation, or it may represent an average level or activity at two or more timepoints before neuromodulation. In some embodiments, the baseline value is a target biomarker level or activity immediately before neuromodulation (e.g., after the patient has already been catheterized). Alternatively, the baseline value for a particular target biomarker may be derived from a standard value for that target biomarker across the population as a whole or across a particular subpopulation. Such a derived baseline value can also be stored in the memory of the analyzer 120 and/or the console 132.

After the neuromodulation and sampling assembly 102 is adequately positioned in the vessel or lumen, the neuromodulation element 200 can be used to purposefully apply or withdraw energy to or from the tissue to induce one or more desired neuromodulating effects on localized regions of the renal artery and adjacent regions of the renal plexus (RP), which lay intimately within, adjacent to, or in close proximity to the adventitia of the renal artery (RA). During and/or after the application of energy, the system 100 can detect changes in the level or activity of one or more target biomarkers associated with neuromodulation and provide real-time or relatively contemporaneous feedback of neuromodulation efficacy.

Before, during, and/or after the energy delivery or withdrawal, the occlusion member 218 carried by the occlusion element 204 of the neuromodulation and sampling assembly 102 can be inflated and/or expanded to at least partially occlude the vessel or lumen proximal to the treatment site, as shown in FIG. 6D (the direction of blood flow is indicated by arrows "BF"). After the occlusion member 218 is inflated and/or expanded, a negative pressure source can be activated to draw a post-neuromodulation sample proximally through the sampling port 108 and sampling lumen 400 to a proximal portion 114 of the treatment device 110 (e.g., the handle 112). Occlusion of the vessel or lumen upstream of the treatment site is expected to isolate and/or preserve target biomarkers released into the vessel or lumen as a result of the neuromodulation. Additionally, full or partial occlusion can cause pooling of the blood in the vessel or lumen distal to the occlusion member 218 that facilitates collection of a sufficient sample size (e.g., 1-5 cc) for subsequent analysis. In some embodiments, a sufficient sample size volume can be significantly smaller (e.g., less than about 1 cc). For example, the sampling lumen 400 may include an in vivo sensor (described below) and/or test element (described below) that can detect biomarker levels in sample volumes less than about 1 cc. Because the average renal artery contains about 1 cc of collectable biological sample, the occlusion member 218 may remain in a fully or partially inflated and/or expanded state for about 1 to 5 minutes before collection to allow sufficient pooling of the biological sample in the renal artery. Alternatively, in some embodiments, collection of a sample can occur during or after neuromodulation without use of an occlusion member 218. In these cases, the sampling element 202 can be distal to the neuromodulation element 200 so as to be downstream of the treatment site with respect to blood flow and more likely to collect target biomarkers resulting from the neuromodulation.

In some embodiments, collection of the post-neuromodulation sample can include an iterative process of inflating and/or expanding the occlusion member 218, collecting a first quantity of the sample, partially deflating the occlusion member 218 to allow perfusion of the renal artery, then re-inflating and/or re-expanding the occlusion member 218 to collect a second quantity of the sample. Such an iterative process can be used to collect any desired number of sample quantities until a sufficient sample volume has been reached. As discussed above, inflation and deflation of the occlusion member 218 can be automatically or manually controlled to achieve a desired occlusion to perfusion ratio. In some embodiments, the therapeutic element 502 can be configured to radially expand into a deployed state 504 at the treatment location.

Figure 7:
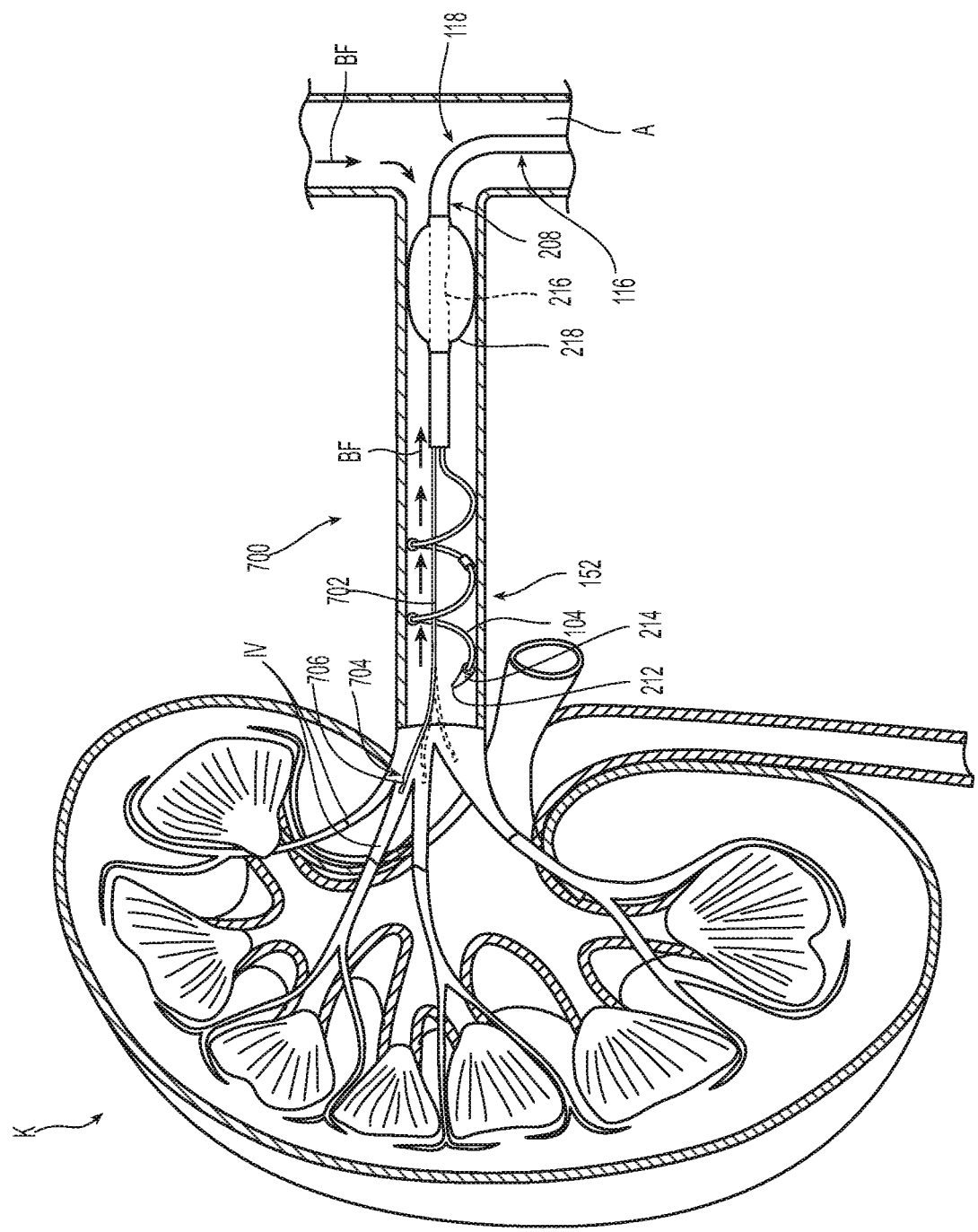
FIG. 7 is a cross-sectional view of the neuromodulation and sampling assembly shown in FIG. 2A including a sampling extension within a renal artery in accordance with an embodiment of the present technology.

FIG. 7 is a side view illustrating a neuromodulation and sampling assembly 700 configured in accordance with another embodiment of the present technology. As shown, the sampling element of the neuromodulation and sampling assembly 700 can include a sampling extension 702 configured to distally extend into an interlobar vessel IV (e.g., an interlobar artery (shown) and/or interlobar vein) of a kidney K of the patient. It is believed that kidney K tissue may contain higher concentrations of target biomarkers than arterial blood. For example, in some embodiments the sampling extension 702 can include an elongated tubular shaft slidably positioned within the sampling lumen 400. The sampling extension 702 can have a sampling port 706 at a distal section 704 configured to be positioned within or at least proximate to an interlobar vessel IV of a kidney. A proximal region (not shown) of the sampling extension can be located at the handle 112 and can be manipulated to displace (e.g., move proximally, move distally, bend, deflect, etc.) the distal section 704 of the sampling extension 702. For example, in some embodiments, the sampling extension can be extended and/or retracted while the occlusion member 218 at least partially occludes the renal artery RA.

FIG. 8 is a side view illustrating a neuromodulation and sampling assembly 800 configured in accordance with another embodiment of the present technology. FIG. 9 is a cross-sectional end view taken along line 9-9 in FIG. 8. Referring to FIGS. 8 and 9 together, the neuromodulation and sampling assembly 102 may include a perfusion intake 802 proximal to the occlusion member 218, a perfusion outlet 804 distal to the occlusion member 218, and a perfusion lumen 900 extending between the perfusion intake and the perfusion outlet. In some embodiments, a pressurization device 902 (e.g., an impeller or a pump) can be used to move blood through the perfusion lumen via the perfusion intake and out of the perfusion lumen via the perfusion outlet.

The devices, systems and methods for conveying the post-neuromodulation sample from the sampling port 108 to an analyzer 120 and for analyzing the post-neuromodulation sample can be the same as that described above with respect to the baseline or pre-neuromodulation sample. Once determining the post-neuromodulation target biomarker level or activity, the processing circuitry associated with the analyzer 120, handle 112, and/or console 132 can compare the post-neuromodulation biomarker level or activity to the baseline level or activity and provide real-time or relatively contemporaneous feedback (e.g., auditory or visual) to the practitioner as to the efficacy of the neuromodulation. For example, target biomarkers for use in the methods disclosed herein may exhibit a change (e.g., a two-fold or greater, a three-fold or greater, a five-fold or greater, or a ten-fold or greater change) in level or activity in response to neuromodulation. If the feedback indicates that a neuromodulation treatment has not been effective, the neuromodulation element 200 can be re-activated (e.g., shifted and then reactivated) to perform a second neuromodulation. Once the second neuromodulation treatment is complete, an additional post-neuromodulation sample can be collected and analyzed to determine whether or not to continue treatment. This process can be repeated until sufficient neuromodulation has been effectuated at the treatment site.

In some embodiments of the methods disclosed herein, renal neuromodulation efficacy can be determined by detecting changes in the level or activity of a single target biomarker. In other embodiments, efficacy is evaluated by detecting changes in the level or activity of two or more target biomarkers. In some of these embodiments, neuromodulation is classified as successful if each of the target biomarkers exhibits a change in level or activity. In other embodiments, neuromodulation is classified as successful if a threshold number or a specific subset or combination of target biomarkers exhibits a change in level or activity. In embodiments that utilize two or more target biomarkers, the target biomarkers may be all proteins, all non-proteins, or a combination of proteins and non-proteins.

Target biomarkers for use in the methods disclosed herein can exhibit a change in level or activity within a predetermined timeframe post-neuromodulation. In certain embodiments, the methods provided herein allow for real-time or relatively contemporaneous monitoring of renal neuromodulation efficacy. Accordingly, certain target biomarkers for use in the methods disclosed herein may exhibit a change in level or activity at the time of neuromodulation or relatively contemporaneous to neuromodulation. For example, in certain embodiments a target biomarker exhibits a change in level or activity within 1 minute, 2 minutes, 5 minutes, 10 minutes, 15 minutes, or 30 minutes of neuromodulation. Accordingly, in certain embodiments, post-neuromodulation level or activity for a target biomarker is determined during neuromodulation or relatively contemporaneous to neuromodulation (e.g., within 1 minute, 2 minutes, 5 minutes, 10 minutes, 15 minutes, or 30 minutes of neuromodulation). In some embodiments, a post-neuromodulation level or activity for a target biomarker is determined in an acute timeframe (e.g., while the subject is still catheterized and/or under anesthesia). Alternatively or in addition to a change in level or activity at the time of neuromodulation or relatively contemporaneous to neuromodulation, a target biomarker may exhibit a change in level or activity at a later timepoint (e.g., at a chronic timepoint). For example, in certain embodiments a target biomarker exhibits a change in level or activity within 2 hours, 4 hours, 6 hours, 8 hours, 12 hours, 24 hours, 48 hours, 72 hours, 7 days, 14 days, one month, two months, four months, or one year of neuromodulation. Accordingly, in certain embodiments, post-neuromodulation level or activity for a target biomarker is determined 2 hours or more after neuromodulation (e.g., within 4 hours, 6 hours, 8 hours, 12 hours, 24 hours, 48 hours, 72 hours, 7 days, 14 days, one month, two months, four months, or one year of neuromodulation). In certain embodiments, changes in target biomarker level or activity at these later timepoints can be used to assess or classify a subject's response to neuromodulation. The resultant information can be used to develop predictive models for determining whether neuromodulation is likely to be effective in a particular subject or subpopulation.

In certain embodiments, the methods provided herein can produce a biofeedback score that indicates to a physician the likelihood that a neuromodulation procedure was successful. In these embodiments, a biofeedback score falling within a certain range may indicate that the procedure was likely successful, while a score falling outside this range indicates that the procedure was unsuccessful. In other embodiments, the methods provided herein provide a binary "yes or no" indicator of the success of a neuromodulation procedure. In these embodiments, a specific threshold increase or decrease in the level or activity of a target biomarker or set of target biomarkers may indicate the neuromodulation procedure was successful. For example, the specific threshold change may indicate that the neuromodulation procedure was successful with a specific confidence interval (e.g., 95% or greater, 97% or greater, or 99% or greater). Information regarding changes in the level or activity of a target biomarker may be combined with one or more additional parameters, such as temperature or impedance in assessing neuromodulation efficacy. For example, efficacy may be evaluated based on a combination of all parameters, with changes in target biomarker level or activity simply functioning as one of the parameters.

Figure 10:
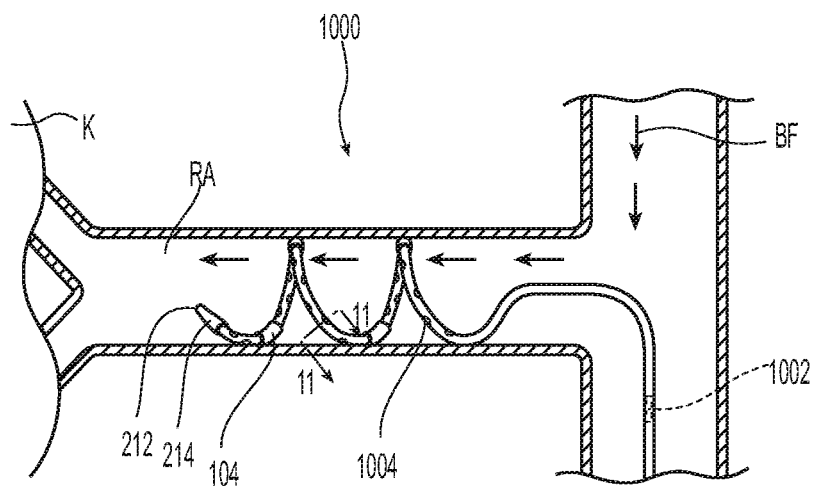
FIG. 10 is a cross-sectional view of a neuromodulation and sampling assembly in accordance with an embodiment of the present technology.
Figure 11:
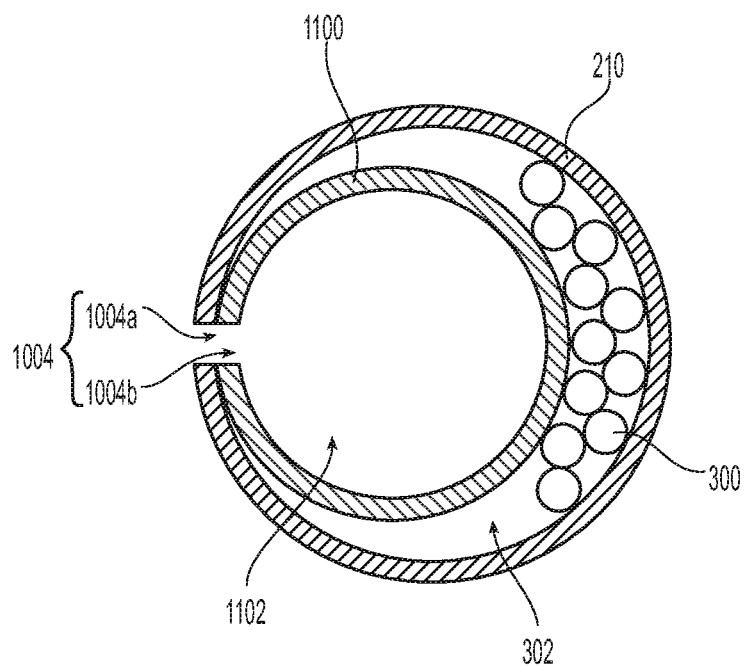
FIG. 11 is a cross-sectional end view taken along line 11-11 in FIG. 10.

FIG. 10 is an elevational view of another embodiment of a neuromodulation and sampling assembly 1000 configured in accordance with the present technology. FIG. 11 is a cross-sectional end view taken along line 11-11 in FIG. 10. Referring to FIGS. 10 and 11 together, the neuromodulation and sampling assembly 1000 can include the one or more energy delivery elements 104. One or more sampling ports 1004 can be interspersed between the one or more energy delivery elements 104 along the support structure 210 of the neuromodulation and sampling assembly 1000. As shown in FIG. 11, an open center channel 1102 of a control member 1100 may be used as both a guide wire lumen and a sampling lumen, thus reducing the delivery profile of the neuromodulation and sampling assembly 1000. For example, the open center channel 1102 or shared lumen can extend proximally from an opening 212 at a tip 214 of the neuromodulation and sampling assembly 1000.

The support structure 210 and the control member 1100 and can individually have one or more openings 1004a, 1004b, respectively, that can be circumferentially and axially aligned and sealed to form a passageway (e.g., the sampling port 1004) between an interior portion of the vessel and the center channel 1102. The center channel 1102 can be in fluid connection with a negative pressure source (not shown) such as a syringe or a vacuum to facilitate collection of a biological sample through the sampling ports 1004 and/or the distal opening 212 and through the center channel 1102. The center channel 1102 may further include a one-way valve or seal 1002 to reduce or prevent contamination of a proximal portion of the treatment device 110. For example, in some embodiments the seal 1002 can be opened only when subject to a sufficient level of negative pressure such that sample collection would only occur at designated times throughout the neuromodulation. Methods for collection and analysis of the biological sample can be similar to those stated above with reference to FIGS. 1-6D.

Figure 12:
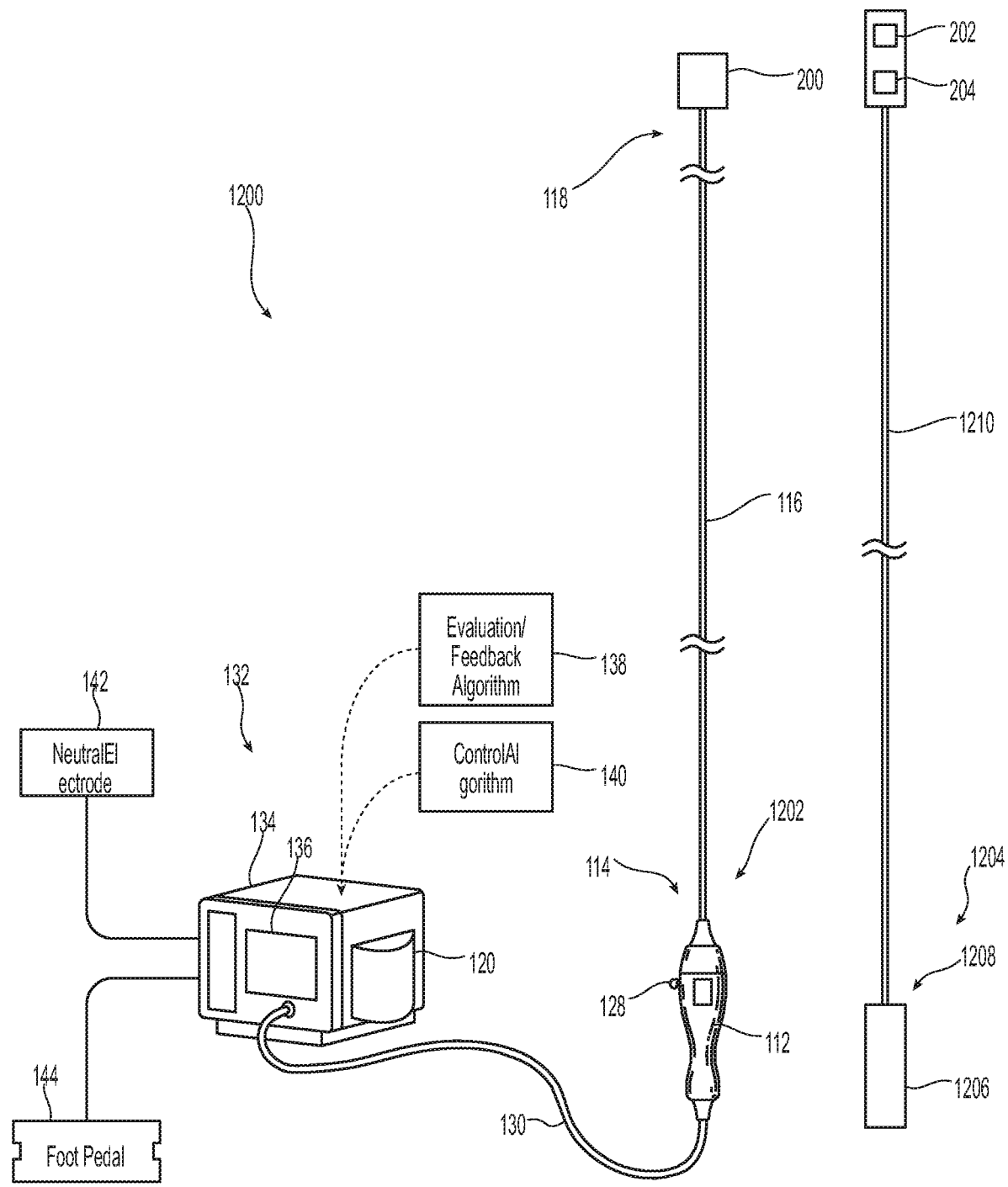
FIG. 12 is a partially-schematic perspective view illustrating a system including a neuromodulation device and a separate sampling device configured in accordance with an embodiment of the present technology.

FIG. 12 is a partially-schematic diagram illustrating another embodiment of a system 1200 that can include a neuromodulation device 1202 (e.g., a catheter) and a separate a sampling device 1204. The neuromodulation device 1202 is generally similar to the previously described treatment device 110 (referenced herein with respect to FIGS. 1-6D). The neuromodulation device 1202, however, does not include the sampling element 202 at a distal portion 118 of the elongated shaft 116. Similar to the treatment device 110, the neuromodulation device 1202 can include a neuromodulation element 200 at the distal portion 118 of the shaft 116. In some embodiments, the sampling device 1204 includes a retrieval portion 1206, a sampling element 202, an occlusion element 204, and an elongated shaft 1210 extending between the retrieval portion 1206 and the sampling element 202 and the occlusion element 204. In some embodiments, the sampling device 1204 can be without the occlusion element 204. The elongated shaft 1210 can be configured to locate the sampling element 202 and the occlusion element 204 intravascularly (e.g., within a renal artery) or within another suitable body lumen (e.g., within a ureter) at a treatment location.

Figure 13A:
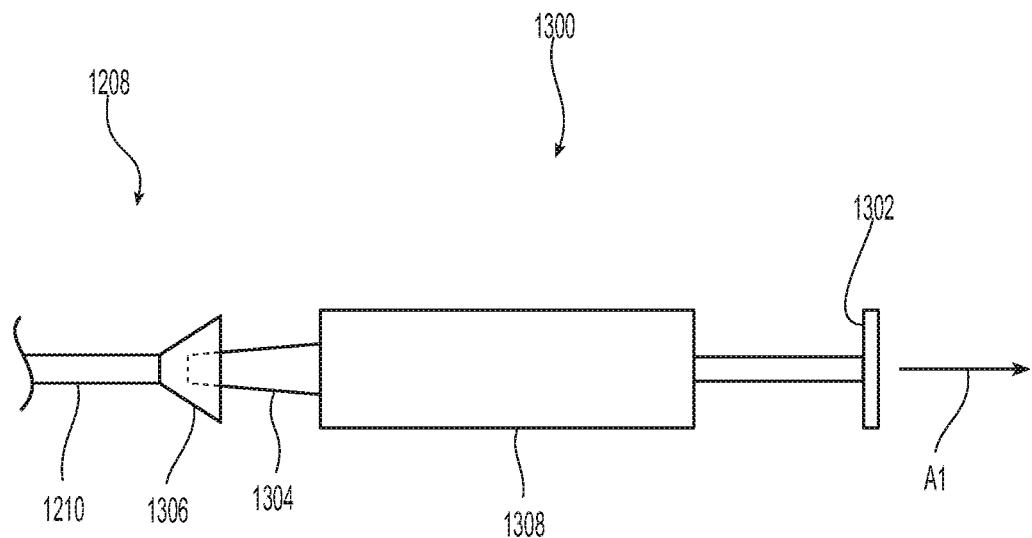
FIGS. 13A-13B are enlarged side views illustrating various embodiments of the retrieval portion of FIG. 12 configured in accordance with the present technology.

The elongated shaft 1210 of the sampling device 1204 can have a sampling lumen (not shown) extending from one or more sampling ports (not shown) of the sampling element 202 to the retrieval portion 1206. The shaft 1210 may further include an inflation lumen 500 extending from one or more inflation openings 216 of the occlusion element 204 to an outlet at a proximal portion 1208 of the shaft 1210. The proximal portion 1208 of the shaft 1210 can have a shaft adapter 1306 (e.g., a luer adapter) (FIG. 13A) configured to receive a retrieval portion adapter 1304 (e.g., a luer adapter, a nozzle, etc.) (FIG. 13A) and form a seal (e.g., a fluid-tight seal, an airtight seal, etc.) with the retrieval portion adapter 1304. FIG. 13A illustrates one embodiment of a retrieval portion 1300 configured in accordance with the present technology. The retrieval portion 1300 can be a syringe that includes a hollow main body 1308 and a plunger 1302. The plunger 1302 can be extended, as indicated by arrow A1, to draw a biological sample into and proximally along the sampling lumen 400, through the retrieval portion adapter 1304 and into the main body 1308. The plunger 1302 can be moved in the opposite direction to expel the sample. For example, the retrieval portion 1300 can be separated from a shaft adapter 1306 and used to transport a collected sample to an analyzer 120 that is part of the console 132. The plunger 1302 can be depressed to deliver the sample to the analyzer 120. In some embodiments, the collected sample can be transport to a standalone analyzer 120 (not shown). The sample can be analyzed using the methods described above with reference to FIGS. 1-6D.

Figure 13B:
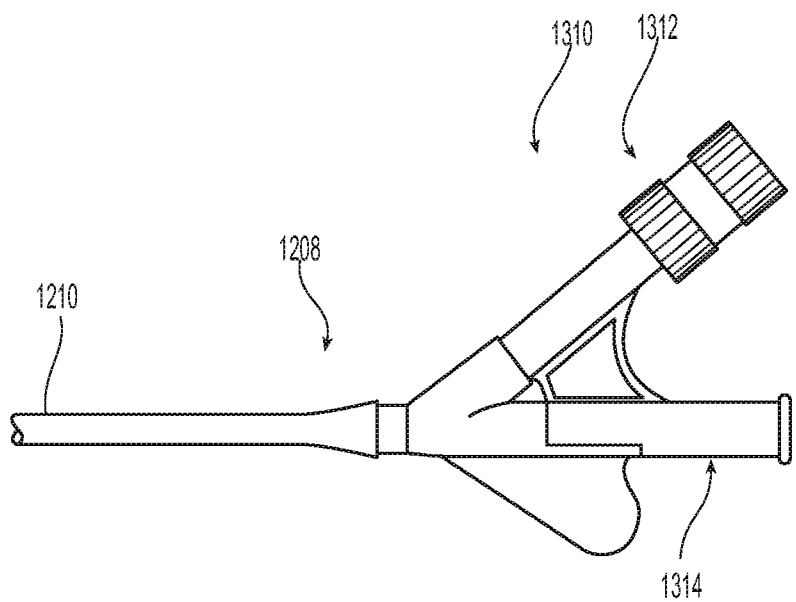

FIG. 13B illustrates another embodiment of a retrieval portion 1310 configured in accordance with the present technology where the retrieval portion 1310 is a hub having a first port 1312 and a second port 1314. For example, the first port 1312 can be configured to connect with the sampling lumen 400 and the second port 1314 can be configured to connect with the inflation lumen. The first port 1312 can further be configured to receive a retrieval device (e.g., a syringe, a vacuum, etc.) (not shown). The second port 1314 can be configured to receive an inflation device (e.g., an automated air or fluid pump) (not shown).

FIG. 14 illustrates another embodiment of a the neuromodulation device 1400 and a sampling device 1402 simultaneously positioned within a vessel (e.g., a renal artery) in accordance with an embodiment of the present technology. FIGS. 15 and 16 are cross-section end views taken along lines 15-15 and 16-16, respectively, in FIG. 14. Referring to FIGS. 14-16 together, the elongated shaft 1210 of the sampling device 1402 can be slidably positioned within the lumen 222 of the neuromodulation device 1400 and has a sampling lumen 1500 therein. A biological sample may be collected through one or more sampling ports 1404 located along a distal portion of the sampling device 1402 and/or an opening 1406 at a distal end of the sampling device 1402. The distal portion of the sampling device 1402 can be moved proximally or distally relative to the neuromodulation device 1400. In some procedures, the neuromodulation device 1400 can be substantially stationary relative to the vessel before, during, and/or after delivering energy (e.g., thermal energy, RF energy, acoustic energy, etc.) to targeted tissue. In some embodiments, the distal portion of the sampling device 1402 can be moved axially to obtain samples at any location while the energy is delivered.

Figure 17:
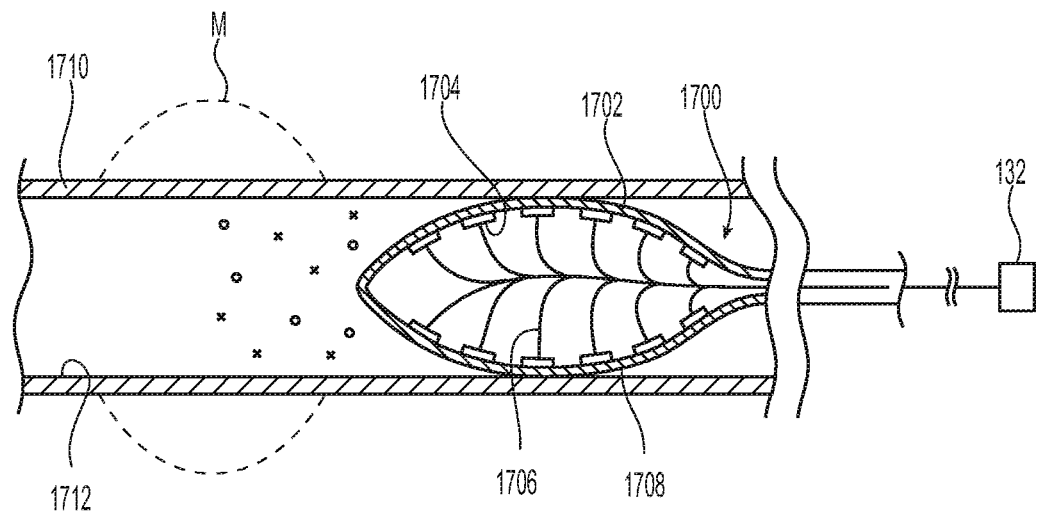
FIG. 17 is an enlarged cross-sectional view of a sensing system configured in accordance with an embodiment of the present technology.

FIG. 17 is a cross-sectional view of an in vivo sensing system 1700 that includes a deployable member 1702 in accordance with an embodiment of the present technology. The member 1702 can be moved from a collapsed configuration to an expanded configuration (as illustrated) and can include one or more detection agents that form at least a portion of an exterior surface 1708. In some embodiments, the member 1702 is in the form of a balloon made of a compliant material (e.g., silicon, an elastomeric polymer, etc.). Connectors 1706 can couple sensors 1704 to a console 132. The sensors 1704 can be configured to detect interaction between the detection agent(s) and biological indicators of interest, such as biomolecules expressed on an interior surface 1712 of a vessel wall 1710, enzymes activated in response to treatment (e.g., ablation), or the like. For example, the detection agent can include an antibody for labeling or coupling to secreted or otherwise released biomolecules. In this manner, biomolecules can be conveniently captured.

To deliver the sensing system 1700, the member 1702 can be in the collapsed configuration for delivery using, for example, a delivery sheath. After the member 1702 is in a desired location, it can be inflated and/or expanded to the illustrated inflated, expanded configuration. The exterior surface 1708 can contact the interior surface 1712 of the wall 1710. When the exterior surface 1708 of the member 1702 is pressed against the wall 1710, the detection agent can capture indicators (e.g., biomolecules, biomarkers, etc.) along the wall 1710. The member 1702 can contact the vessel wall 1710 for at least 5 minutes, 10 minutes, 20 minutes, 30 minutes, or 40 minutes after therapy to allow a desired amount of biomolecules to be expressed on the vessel wall 1710. In some embodiments, the sensing system 1700 can be used days after ablation.

Figure 18:
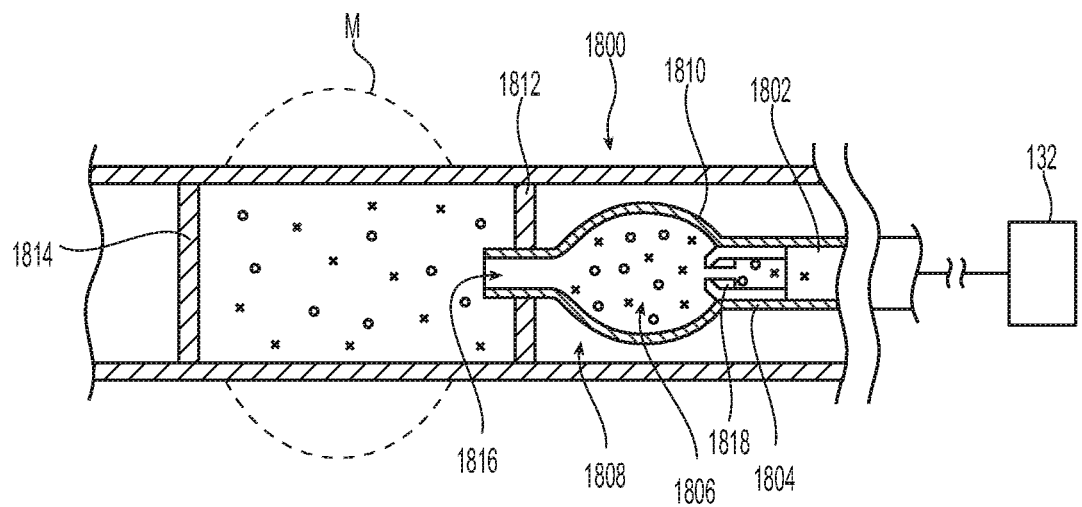
FIG. 18 is an enlarged cross-sectional view of another embodiment of a sensing system configured in accordance with the present technology.

FIG. 18 is an enlarged partial cross-sectional view of another embodiment of an in vivo sensing system 1800 having a sampling assembly 1808 for in vivo analysis in accordance with an embodiment of the present technology. The sampling assembly 1808 includes an expandable member 1810, an inlet conduit 1816, and a sensor 1804. A connector 1802 can provide communication between the sensor 1804 and a console 132. The sensor 1804 can have one or more optical sensing elements, chemical sensing elements, electrical sensing elements, or the like, to send a signal via the connector 1802 to the console 132. The sensor 1804 is positioned to analyze blood that has passed through the inlet conduit 1816 and is contained within a chamber 1806.

In operation, blood flows proximally through the inlet conduit 1816 and into the chamber 1806. The biological sample can include, without limitation, biomolecules secreted or released in response to therapy or expressed molecules activated by enzymes. In the illustrated embodiment, blood can be drawn into the chamber 1806 to increase the concentration of the molecules in the chamber 1806. In some embodiments, the member 1810 can contact and interact with biomolecules on the surface of an artery wall RA to generate an output, as discussed in connection with FIG. 17. In some embodiments, the biomolecules are stored in the chamber 1806 for subsequent detection to enhance protocols and output generation.

An ablation site M can be located between detection or obstructing elements 1814, 1812. The obstructing elements 1814, 1812 can be in the form of a balloon catheter. For example, the obstructing element 1814 can be a distal balloon and the obstructing element 1812 can be a proximal balloon. The illustrate biomolecules can be molecules that were released or secreted by the vessel wall RA in response to the ablation. The inlet conduit 1816 extends through an opening 1812 such that the biomolecules contained between the obstructing elements 1814, 1812 can be drawn into the chamber 1806. A one-way valve 1818 may be positioned between the chamber 1806 and the connector 1802. For removal, the system 1800 can be moved proximally out of the detection or obstructing element 1812.

In some embodiments, the sampling assembly 1808 includes one or more neuromodulation assemblies to perform both neuromodulation and patient sensing. The sensing can be performed before, during, and/or after the neuromodulation procedure. If needed, any number of additional neuromodulation procedures can be performed. The efficacy of the therapy can be assessed using the sampling assembly 1808.

Figure 19:
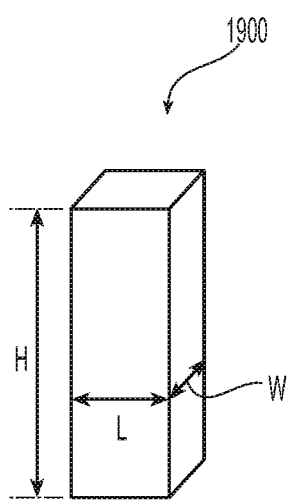
FIG. 19 is an enlarged perspective view of a testing element configured in accordance with an embodiment of the present technology.

FIG. 19 shows an enlarged perspective view of a test element 1900 configured in accordance with an embodiment of the present technology. The test element 1900 can be configured to determine the level or activity of a target biomarker and/or aid in the determination of target biomarker levels in a collected sample. The test element 1900 can have a rectangular cross-section, a circular cross section, and/or any suitable shape and/or size. The test element 1900 can be relatively two-dimensional (e.g., at least one of a length L, width W, or height H of the test element 1900 is less than or equal to 0.10 mm) or in some embodiments the test element is relatively three-dimensional. One or more exterior and/or interior surfaces of the test element 1900 can be coated and/or impregnated with a detection agent and/or capture agent. Capture or detection agents may be immobilized on a surface such as a bead, resin, or one or more surfaces of the test element 1900 and/or on a bead or resin on one or more surfaces of the test element 1900. Examples of suitable resins include, for example, hydrophobic resins, cation/anion exchange resins (e.g., carboxymethyl, sulfopropyl/diethylamine), immobilized metal affinity chromatography (IMAC) resins, and polar chromatographic resins (e.g., silica gel). In those embodiments that utilize a surface such as a bead or resin, all capture agents on the surface may be specific for a single target biomarker. Alternatively, capture or detection agents for multiple target biomarkers may be present on a single surface, allowing for simultaneous detection and analysis of multiple target biomarkers.

Figure 20A:
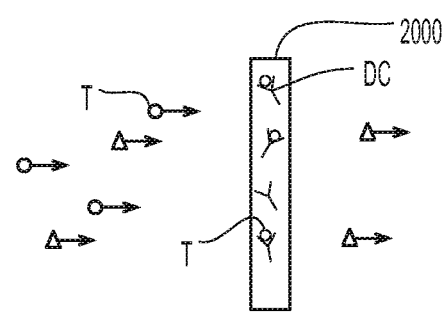
FIG. 20A is a partially schematic view illustrating a trapping test element configured in accordance with an embodiment of the present technology.
Figure 20B:
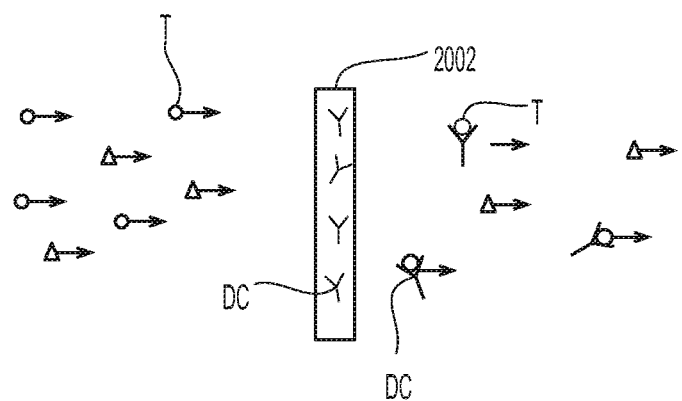
FIG. 20B is a partially schematic view illustrating a tagging test element configured in accordance with an embodiment of the present technology.

In some embodiments the test element 1900 can be penetrable (e.g., a filter through which a biological sample can flow, a latticework having penetrable pores, etc.) and in some embodiments the test element 1900 can be relatively non-penetrable but nonetheless provide a "sticky" surface to which surrounding target biomarkers may be attracted and/or adhere/adsorb. FIG. 20A is a schematic representation of one mode of operation for an embodiment of a "trapping" test element 2000 configured in accordance with the present technology. As shown, in some embodiments the target biomarkers (T) in the surrounding sample may adhere to the detection agent and/or capture agent(s) (collectively labeled DC) coated on the surface of and/or within the infrastructure of the trapping test element 2000. FIG. 20B is a schematic representation of another mode of operation for an embodiment of a "tagging" test element 2002 configured in accordance with the present technology. As shown, in some embodiments the detection and/or capture agents (DC) coated on the surface of and/or within the infrastructure of the tagging test element 2002 can bind or stick to passing and/or nearby target biomarkers (T) thus separating from the tagging test element 2002. The agents DC are then carried by the bound target biomarkers (T) and can likewise be identified during subsequent analysis of the collected sample. In these and other embodiments, the tagging test element 2002 may also be analyzed to determine target biomarker level or activity. Different test elements with different detection and/or capture agents can be used during neuromodulation to assess different target biomarkers.

Figure 21:
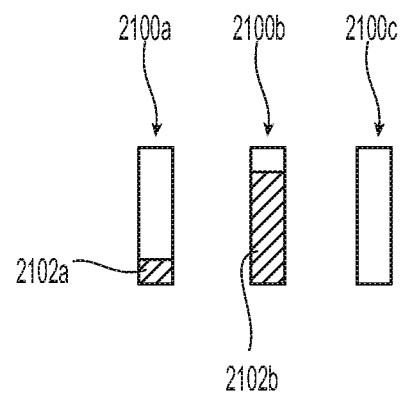
FIG. 21 is a schematic view illustrating a plurality of tagging elements having visual indications configured in accordance with the present technology.
Figure 22A:
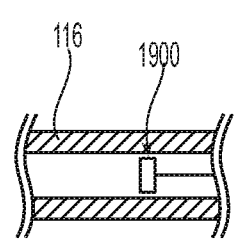
FIGS. 22A-22D are schematic illustrations showing operation of a test element configured in accordance with an embodiment of the present technology.
Figure 22B:
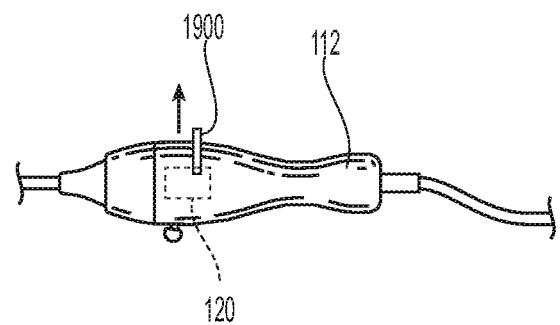
Figure 22C:
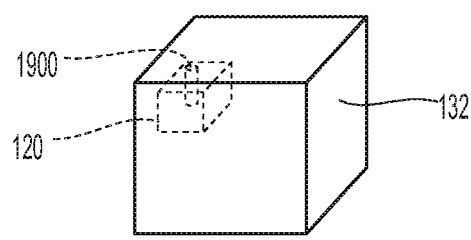
Figure 22D:
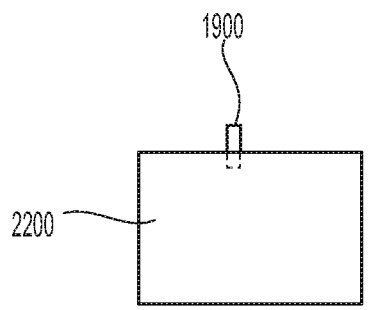

FIG. 21 shows a test element 2100 configured in accordance with another embodiment of the present technology that can be configured to provide a visual indication as to a target biomarker level or activity and/or neuromodulation efficacy. For example, a test element 2100a has a minimal amount of biomolecule or biomarker coverage 2102a indicating a relatively low level of biomolecules or biomarkers. A test element 2100b, for example, has a substantial amount of biomolecule or biomarker coverage 2102b indicating a relatively high level of biomolecules or biomarkers. In some embodiments, a test element 2100c can be a negative control. Test elements that provide a visual indication can be removably positioned within a dynamic flow area (e.g., within the sampling lumen 400 of the shaft 116) and/or within a collected sample having a controlled volume (e.g., within a container in the handle 112, within a container in the console 132, within a standalone container, within an analyzer in the handle 112 or console 132, within a standalone analyzer 120, etc.). After exposure to the sample, the test element 2100 can be separated from the collected sample for visual inspection and analysis, separated from the collected sample for analysis within a separate device, and/or remain within the collected sample for analysis.

In some embodiments, as shown in FIGS. 22A-22D, any of the test elements described above can be utilized within the sampling lumen 400 of the shaft 116 (FIG. 22A) and in some embodiments the test elements can be used in conjunction with an analyzer 120 (e.g., in the handle 112 (FIG. 22B), and/or console 132 (FIG. 22C), a standalone analyzer 2200 (FIG. 22D), etc.) to determine the level or activity of target biomarkers in a sample. After exposure to the sample, the test element 1900 can be separated from the collected sample for analysis within a separate device and/or remain within the collected sample for analysis.

Figure 23:
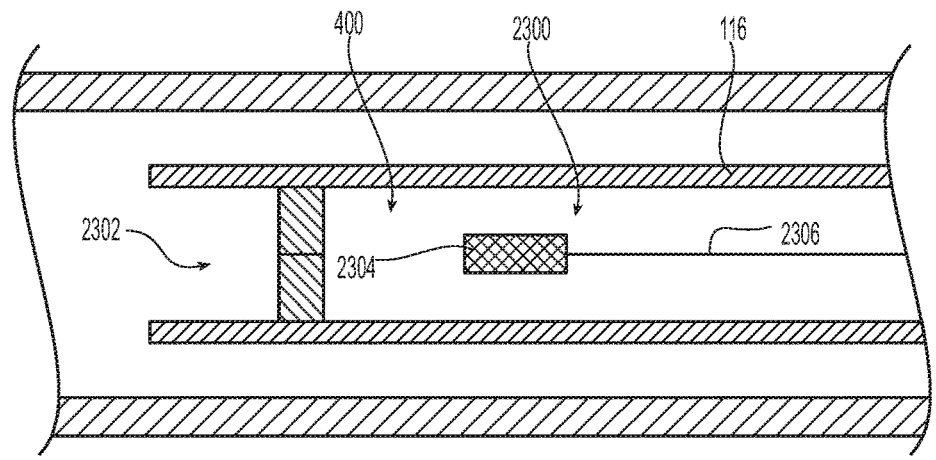
FIG. 23 is a partially schematic cross-sectional view of a test element assembly configured in accordance with an embodiment of the present technology.

FIG. 23 is a cross-sectional view of a portion of a test element assembly 2300 in accordance with an embodiment of the present technology. The test element assembly 2300 includes one or more test elements 2304, an extracorporeal handle (not shown), and a rod 2306 extending between the handle and the test element 2304. The test element assembly 2300 can be slidably positioned within the sampling lumen 400 of a treatment device (shown schematically in FIG. 23 for illustrative purposes). The handle (not shown) of the assembly 2300 can be manipulated to move the rod 2306 and/or test element 2304 distally and proximally along the sampling lumen 400. The sampling lumen 400 can further include a one-way valve 790 or sealing member that allows entry of a sample (but not exit) through a distal opening 2302 of the sampling lumen. Accordingly, the one-way valve prevents detection and/or capture agents integrated with the test element 2304 from entering the bloodstream.

In operation, a vacuum or other negative pressure source can be applied to the sampling lumen 400 causing a biological sample to be drawn proximally through the opening 2302 and one-way valve 790 and be in contact with or close proximity to the test element 2304 (e.g., a trapping 2000 and/or tagging 2002 test element). Once exposed to a sample, the test element assembly 2300 can be: (a) withdrawn proximally through the sampling lumen 400 for removal and visual inspection of the test element 2304 (e.g., a test element with a visual indication) and/or (b) withdrawn proximally for removal and transport to a separate analyzer for analysis at the separate analyzer. During removal of the test element 2304, the shaft 116 can remain positioned within a vessel (e.g., a renal artery) of a patient, or in other embodiments, the shaft 116 and the test element assembly 2300 can be removed simultaneously. The used test element 2304 can be replaced with a fresh test element and/or test element assembly 2300 while the shaft 116 remains positioned within a renal artery of a patient. In some embodiments utilizing a tagging test element, the tagged biological sample can be drawn proximally through the sampling lumen 400 (after exposure to the tagging test element) to an extracorporeal location. Analysis of the tagged sample can be similar to that described above with reference to FIGS. 1-6D.

Figure 24:
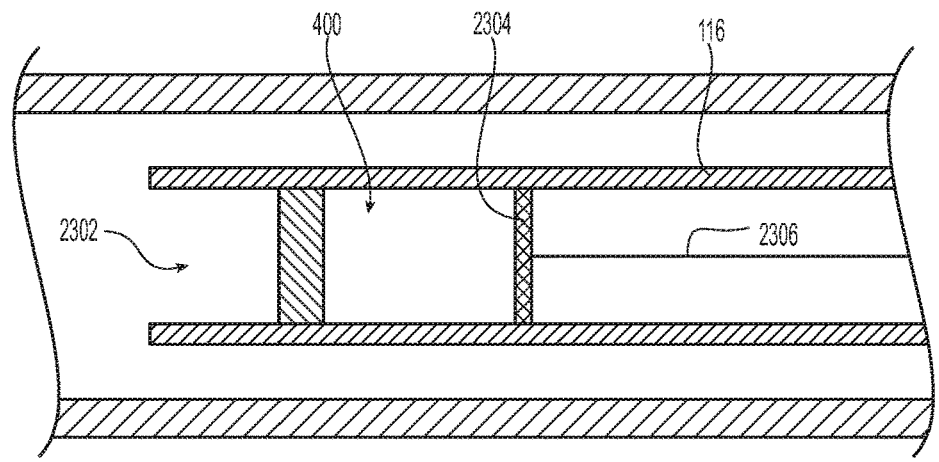
FIG. 24 is partially schematic perspective view of another embodiment of a test element configured in accordance with the present technology.

As shown in FIGS. 23 and 24 together, the test element 2304 for use with the test element assembly 2300 can have any suitable shape, size, and/or orientation to capture and/or tag a passing and/or nearby sample. For example, in FIG. 23, the test element 2304 has an outer cross-sectional area that is approximately the same as or slightly larger than that of the inner cross-sectional area of the sampling lumen 400. The test element 2304 in FIG. 25A can have a relatively short axial length. FIG. 24 shows a test element 2304 having a relatively long axial length and an outer cross-sectional area less than that of the sampling lumen 400 such that a space exists between a test element 2304 surface and an inner surface of the sampling lumen 400. The test element 2304 can generally be shape of a disc (FIG. 24), a cylinder (FIG. 23) or any suitable shape for making contact with a passing and/or nearby sample.

Figure 25:
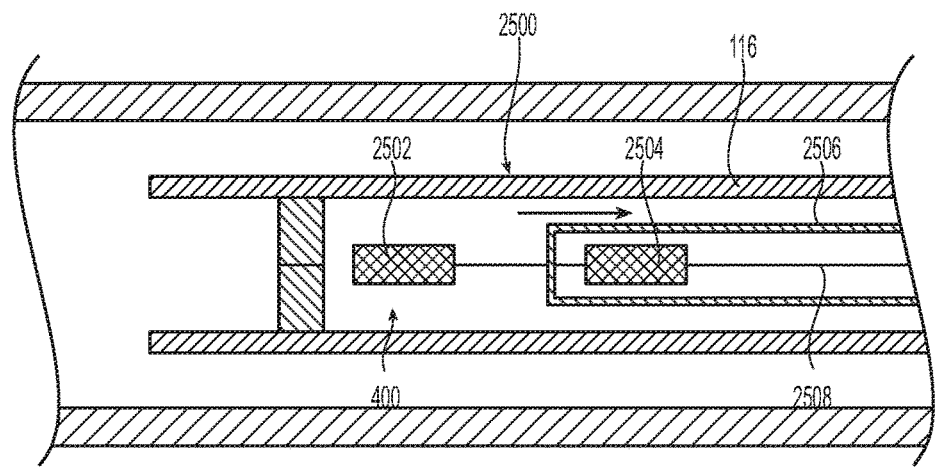
FIG. 25 is a partially schematic cross-sectional view of a test element assembly configured in accordance with an embodiment of the present technology.

FIG. 25 shows a test element assembly 2500 configured in accordance with another embodiment of the present technology can include more than one test element positioned at various locations along a rod 2508 and/or sampling lumen 400, as shown in. In some cases, a plurality of test elements can be spaced apart from one another to allow the blood to flow sequentially through the test elements. The first test element 2502 and the second test element 2504 can be simultaneously exposed to a sample, and in some embodiments the test element assembly 2500 can include a shielding element 2506 configured to selectively expose all or portions of the individual test elements. For example, the test element assembly 2500 can have a first test element 2502 for a first sample and a second test element 2504 for a second sample. As shown in FIG. 25, the second test element 2504 can be positioned within the shielding element 2506 such that a sample moving through the sampling lumen 400 can be in contact with the first test element 2502 but not the second test element 2504 (e.g., to determine a first measurement, to determine a pre-neuromodulation target biomarker level, etc.). Subsequently, the shielding element 2506 can be moved proximally (see arrow A2) to expose the second test element 2504 to a nearby sample (e.g., to determine second measurement, to determine a post-neuromodulation biomarker level, etc.). In some embodiments, the first test element 2502 can be removed from the sampling lumen 400 independently of the second test element 2504, and in other embodiments the first test element 2502 and the second test element 2504 can be removed simultaneously. Furthermore, the first test element 2502 and the second test element 2504 can be positioned along the same rod or one or more separate rods (not shown).

In some embodiments, the test element and/or test element assembly can be utilized for in vivo biomarker analysis. For example, the test element assembly can have a sensor (not shown) that can determine whether the target biomarkers have been coupled to the test element based at least in part on, for example, colorimetric signals, fluorescence, energy changes (e.g., heat transfer), electric stimuli, or the like. The sensor (not shown) can send signals to the console 132 via a connector 130, such as a signal wire that is welded, soldered, crimped, and/or otherwise connected to the shaft 116. The connector 130 can extend through the shaft 116 beyond the proximal portion 114 of the treatment device 110 where it can be operatively connected to the console 132 in the form of signal processing equipment suitable for nerve stimulation. For example, the console 132 can include a NIM-Response™ Nerve Integrity Monitor ("NIM"), available from Medronic Xomed of Jacksonville, Fla. In other embodiments, the connector 130 includes one or more optical fibers that send output/signals from the sensor (not shown) and/or biomolecules interacting with detection agents to the console 132.

In other embodiments, the test element assembly can have a multi-layer construction Each layer can have a different detection agent in order to label the different biomolecules. In other embodiments, the test element assembly has a single layer construction. The length of the test element in the direction of the longitudinal axis of the shaft 116 can be increased or decreased to control the amount of time that the sample contacts the test element.

Figure 26A:
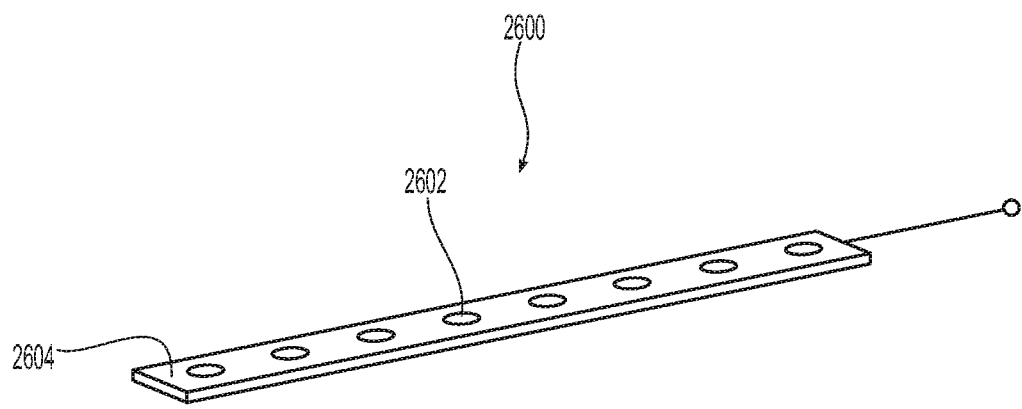
FIGS. 26A and 26B are perspective views of various embodiments of a test element assembly configured in accordance with the present technology.
Figure 26B:
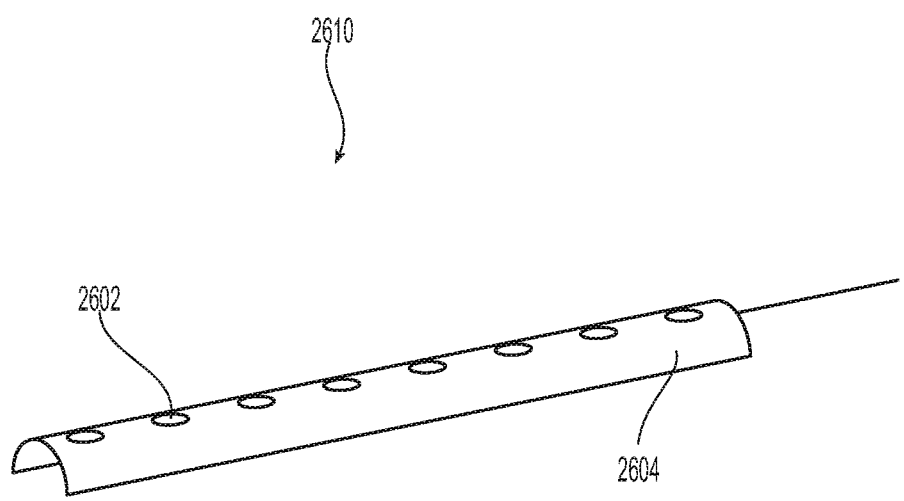

Referring to FIGS. 26A and 26B, in some embodiments, a test element 2600 can include an array of detection features 2602 (e.g., wells, sensors, reservoirs, or the like). As shown in FIG. 26B, a substrate 2604 can be flexible to bend and fit into relatively small lumens yet maintain a sufficiently large surface area for the detection features 2602. In some embodiments, the detection features 2602 can include reservoirs containing one or more detection and/or capture agents (e.g., labels). Any suitable number of detection features 2602 and patterns and configurations can be used.

Figure 27A:
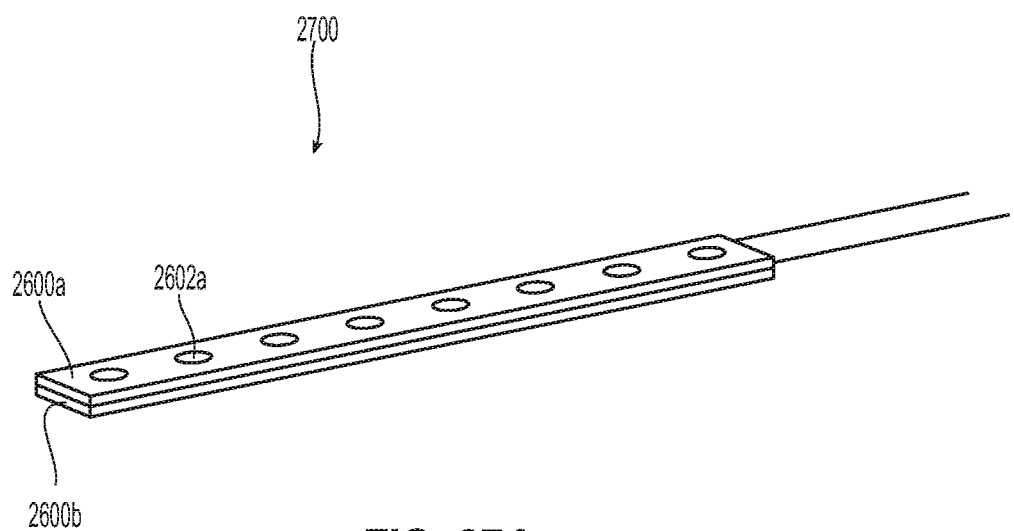
FIGS. 27A and 27B are perspective views of various embodiments of a test element assembly having more than one test element configured in accordance with the present technology.
Figure 27B:
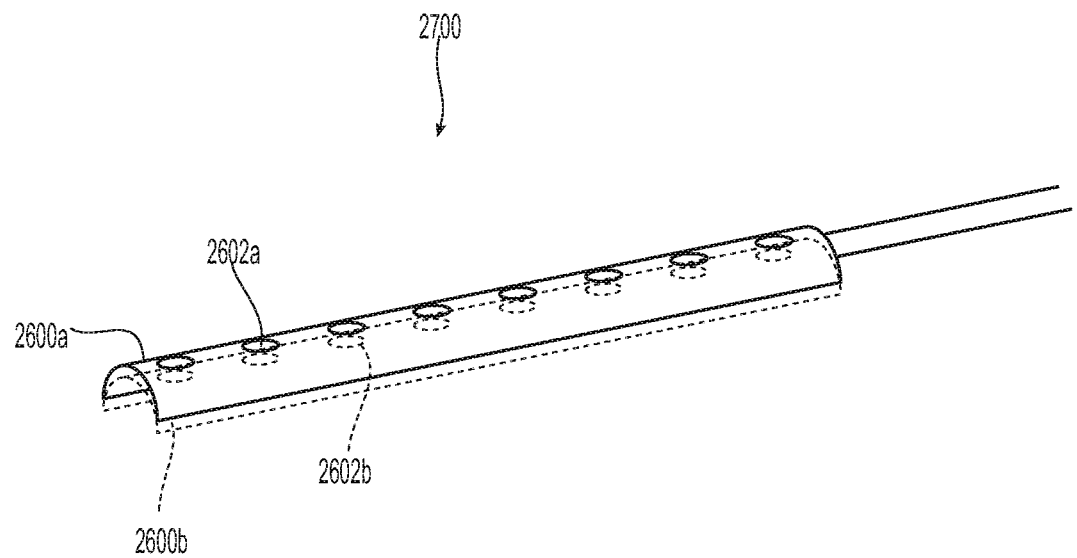

In some embodiments, the test element assembly one or more test elements can be stacked upon one another to deliver a series of labels to the passing and/or nearby sample therethrough and/or expose select regions of individual test elements to a nearby sample. For example, as shown in FIGS. 27A and 27B, the test element assembly 2700 can have a first test element 2600a and a second test element 2600b. When a sample is allowed to flow into the sampling lumen 400, only the detection features 2602a on the first test element 2600a will be exposed to the sample. The first test element 2600a can be removed from the sampling lumen 400 independently of the second test element 2600b, thereby exposing the previously covered detection features 2602b of the second test element 2600b. For example, the first test element 2600a may be used to determine a baseline or pre-neuromodulation biomarker level and the second test element 2600b may be used to determine a post-neuromodulation biomarker level.

III. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal neuromodulation. For example, as mentioned previously, several properties of the renal vasculature may inform the design of treatment devices and associated methods for achieving renal neuromodulation, and impose specific design requirements for such devices. Specific design requirements may include accessing the renal artery, ureter, or renal pelvic anatomy, facilitating stable contact between a therapeutic element of a treatment device and a luminal surface or wall, and/or effectively modulating the renal nerves using the therapeutic element.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS extend through tissues in almost every organ system, providing at least some regulatory function to characteristics as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 28:
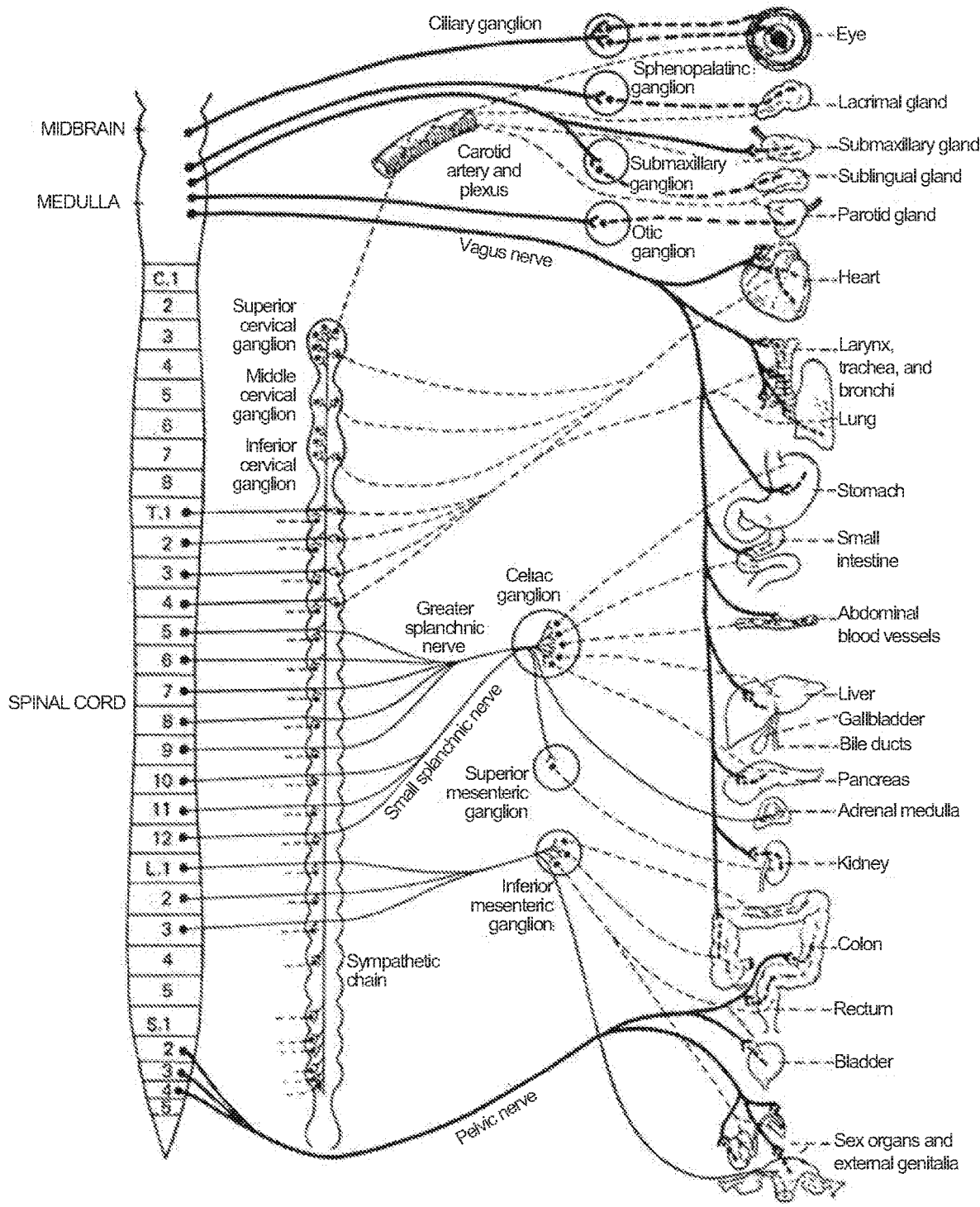
FIG. 28 is a conceptual diagram illustrating the sympathetic nervous system and how the brain communicates with the body via the sympathetic nervous system.

As shown in FIG. 28, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which send sympathetic nerve fibers to the head and thorax organs, and the celiac and mesenteric ganglia (which send sympathetic fibers to the gut).

2. Nerves of the Kidneys

Figure 29:
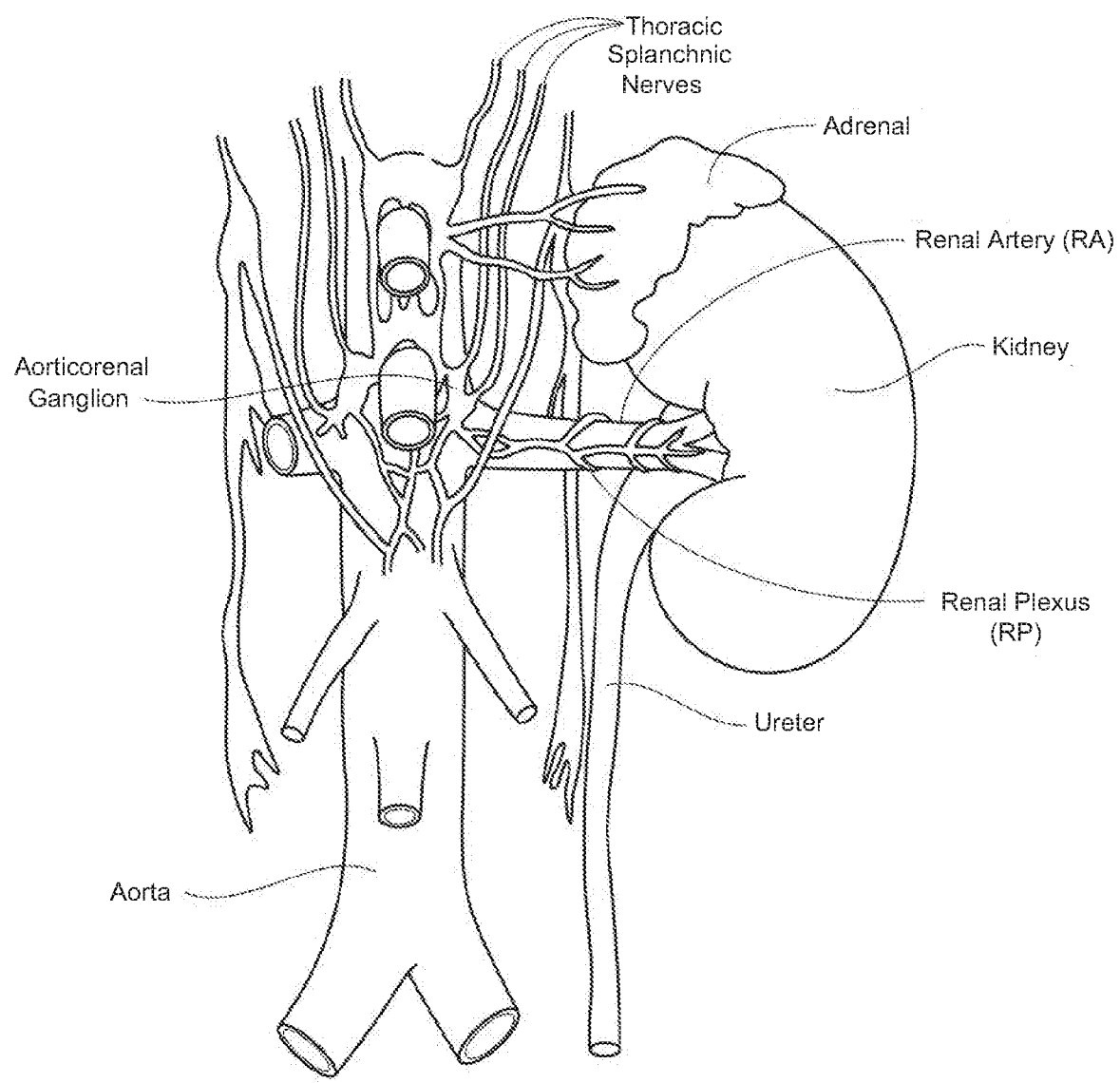
FIG. 29 is an enlarged anatomical view illustrating nerves innervating a left kidney to form a renal plexus surrounding a left renal artery.

As shown in FIG. 29, the kidney neural system includes the renal plexus, which is intimately associated with the renal artery. The renal plexus is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus, also referred to as the renal nerve, is predominantly comprised of sympathetic components. There is no (or at least very minimal) parasympathetic neural activity of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate, widen bronchial passages, decrease motility (movement) of the large intestine, constrict blood vessels, increase peristalsis in the esophagus, cause pupil dilation, piloerection (goose bumps) and perspiration (sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

i. Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

ii. Renal Sensory Afferent Nerve Activity

Figure 30A:
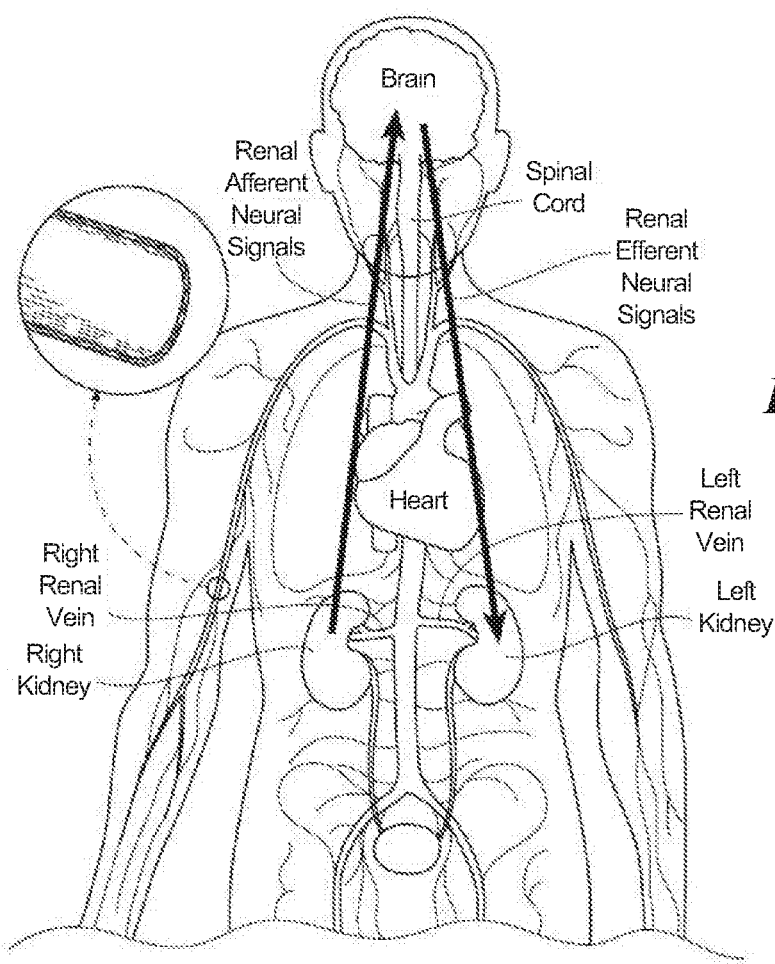
FIGS. 30A and 30B are anatomical and conceptual views, respectively, illustrating a human body including a brain and kidneys and neural efferent and afferent communication between the brain and kidneys.
Figure 30B:
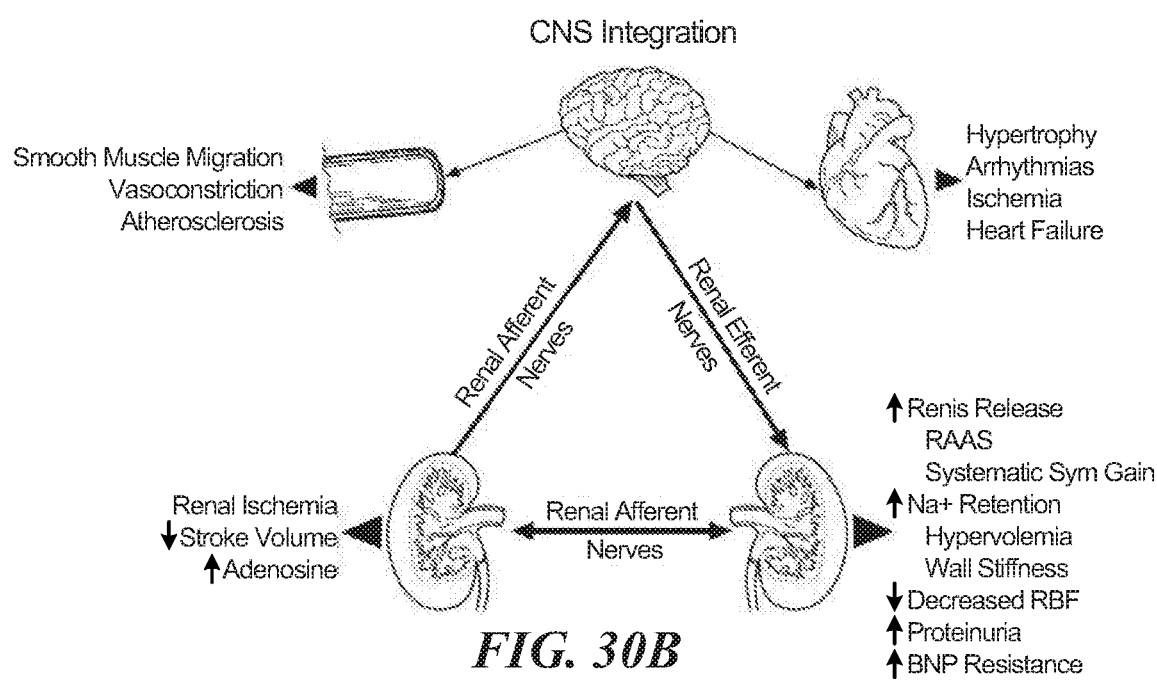

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine may trigger activation of afferent neural communication. As shown in FIGS. 30A and 30B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, fluid volume retention, and vasoconstriction. Central sympathetic over activity also impacts other organs and bodily structures having sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, sodium retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal neuromodulation, a desirable reduction of central sympathetic outflow to various other organs such as the heart and the vasculature is anticipated.

B. Additional Clinical Benefits of Renal Neuromodulation

As provided above, renal neuromodulation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal neuromodulation might also be useful in treating other conditions associated with systemic sympathetic hyperactivity. Accordingly, renal neuromodulation may also benefit other organs and bodily structures having sympathetic nerves, including those identified in FIG. 28.

C. Achieving Intravascular Access to the Renal Artery

Figure 31A:
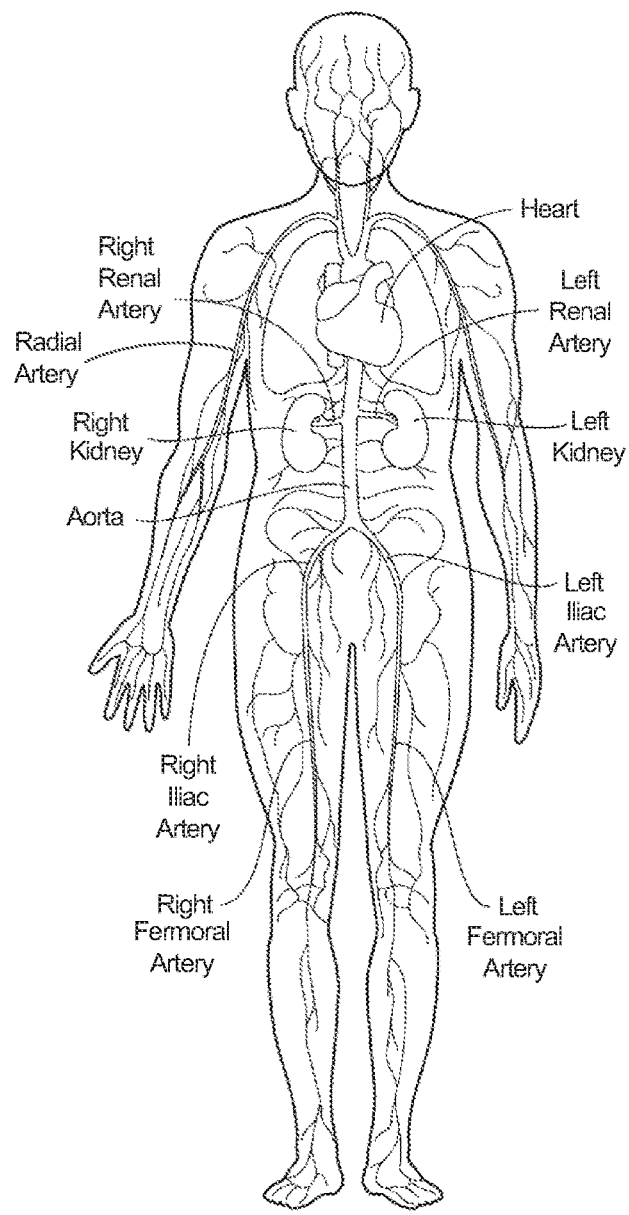
FIGS. 31A and 31B are anatomic views illustrating, respectively, an arterial vasculature and a venous vasculature of a human.

In accordance with the present technology, neuromodulation of a left and/or right renal plexus RP, which is intimately associated with a left and/or right renal artery, may be achieved through intravascular access. As FIG. 31A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 31B:
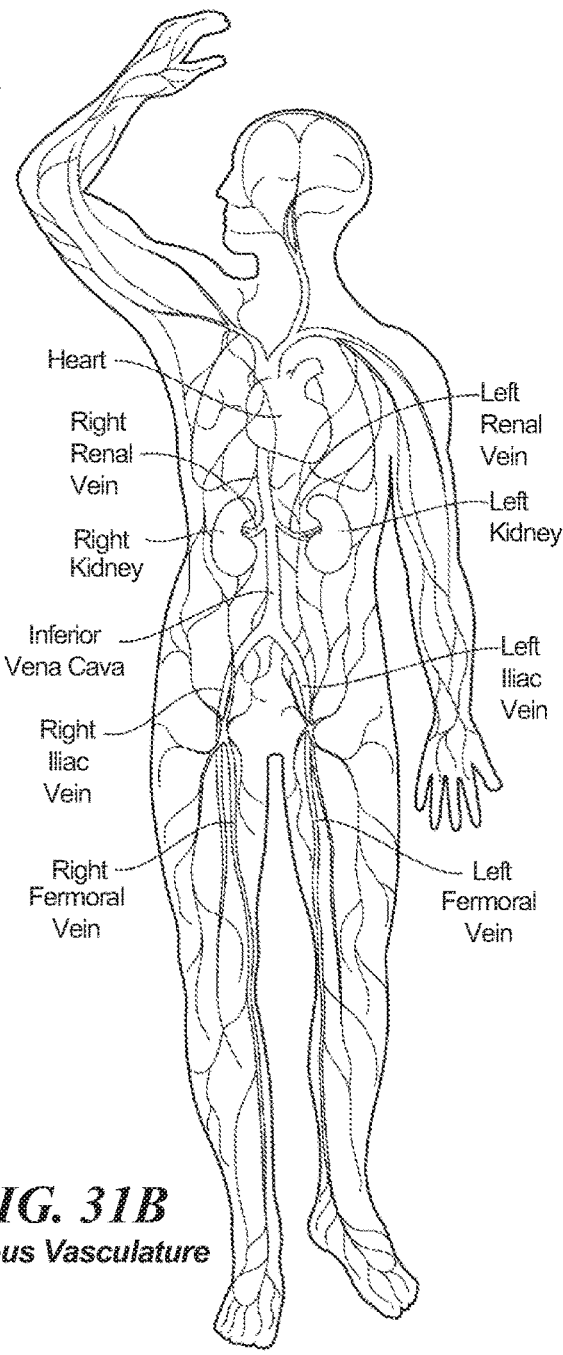

As FIG. 31B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall can be important for predictability. However, navigation typically is impeded by the tight space within a renal artery, as well as tortuosity of the artery. Furthermore, establishing consistent contact can be complicated by patient movement, respiration, and/or the cardiac cycle. These factors, for example, may cause significant movement of the renal artery relative to the aorta, and the cardiac cycle may transiently distend the renal artery (i.e., cause the wall of the artery to pulse).

After accessing a renal artery and facilitating stable contact between neuromodulatory apparatus and a luminal surface of the artery, nerves in and around the adventitia of the artery can be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy can be delivered to the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Accordingly, the complex fluid mechanics and thermodynamic conditions present in the renal artery during treatment, particularly those that may impact heat transfer dynamics at the treatment site, may be important in applying energy from within the renal artery.

The neuromodulatory apparatus can be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to reduce the likelihood of injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, depending on the apparatus, systems, and methods utilized to achieve renal neuromodulation, such properties of the renal arteries also may guide and/or constrain design characteristics.

As noted above, an apparatus positioned within a renal artery can conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment can be important to reach the target neural fibers, the treatment can be prevented from becoming too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4 inches cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IV. Further Examples

The following examples are illustrative of several embodiments of the present technology:

1. A system, comprising:
   a neuromodulation element configured to modulate nerves at or otherwise proximate to a renal artery of a patient;
   an elongated shaft having a first portion configured to be intravascularly positioned while the neuromodulation element modulates the nerves, and a second portion proximal to the first portion, the second portion configured to be extracorporeally positioned while the neuromodulation element modulates the nerves;

an occlusion member extending around a segment of the first portion;
a sampling port distal to the segment of the first portion;
a sampling lumen extending from the sampling port toward the second portion;
an inflation opening within the occlusion member; and
an inflation lumen extending from the inflation opening toward the second portion.

2. The system of example 1, further comprising an analyzer configured to analyze a biological sample from the patient for a biological parameter that changes in response to modulating the nerves.

3. The system of example 2 wherein:
the analyzer is operably connected to the second portion; and
the sampling lumen extends from the sampling port along the shaft to the analyzer.

4. The system of example 2 or example 3, further comprising a handle coupled to the second portion, wherein the analyzer is carried by the handle.

5. The system of any one of examples 2 to 4 wherein the analyzer includes an indicator configured to indicate a status of the biological parameter, a status of modulation of the nerves based on the biological parameter, or both.

6. The system of any one of examples 2 to 5, further comprising:
a perfusion intake proximal to the occlusion member;
a perfusion outlet distal to the occlusion member;
a perfusion lumen extending between the perfusion intake and the perfusion outlet; and
a pressurized device operably connected to the perfusion lumen, the pump configured to move blood into the perfusion lumen via the perfusion intake and out of the perfusion lumen via the perfusion outlet while the occlusion member at least partially occludes the renal artery.

7. The system of any one of examples 1 to 6, further comprising a guide wire lumen within the shaft, wherein the sampling and inflation lumens are positioned within the shaft at least proximate to opposite sides of the guide wire lumen.

8. The system of any one of examples 1 to 7 wherein the occlusion member is a compliant balloon.

9. The system of any one of examples 1 to 8, further comprising a vacuum pump operably connected to the sampling lumen.

10. The system of any one of examples 1 to 9 wherein the neuromodulation element includes a plurality of electrodes spaced apart from one another, the electrodes configured to simultaneously deliver RF energy to the nerves.

11. The system of example 10 wherein:
the neuromodulation element has a delivery state and a deployed state; and
at least a portion of the neuromodulation element is helical in the deployed state.

12. The system of any one of examples 1 to 9 wherein neuromodulation element includes a single electrode.

13. A system, comprising:
a neuromodulation element configured to modulate nerves at or otherwise proximate to a renal artery of a patient;
an elongated shaft having a first portion configured to be intravascularly positioned while the neuromodulation element modulates the nerves, and a second portion proximal to the first portion, the second portion configured to be extracorporeally positioned while the neuromodulation element modulates the nerves;
an occlusion member extending around a segment of the first portion;
a sampling port distal to the segment of the first portion;
a sampling lumen extending from the sampling port toward the second portion;
an inflation opening within the occlusion member;
an inflation lumen extending from the inflation opening toward the second portion;
an analyzer configured to analyze a biological sample from the patient for a biological parameter that changes in response to modulating the nerves;
a sampling extension having a distal sampling element, wherein the sampling extension is configured to distally extend from the shaft beyond the neuromodulation element into an interlobar vessel of a kidney of the patient while the occlusion member at least partially occludes the renal artery; and
the sampling port is carried by the distal sampling element.

14. The system of example 13, further comprising a handle coupled to the second portion, wherein the analyzer is carried by the handle.

15. The system of example 14 wherein the analyzer includes an indicator configured to indicate a status of the biological parameter, a status of modulation of the nerves based on the biological parameter, or both. 16. A system, comprising:
an neuromodulation element configured to modulate nerves at or otherwise proximate to a renal artery of a patient;
a first elongated shaft having a first portion configured to be intravascularly positioned while the neuromodulation element modulates the nerves, and a second portion proximal to the first portion, the second portion configured to be extracorporeally positioned while the neuromodulation element modulates the nerves;
an occlusion member extending around a segment of the first portion;
a sampling port distal to the segment;
a sampling lumen extending from the sampling port toward the second portion;
an inflation opening within the occlusion member;
an inflation lumen extending from the inflation opening toward the second portion;
a second elongated shaft having a distal end portion coupled to the neuromodulation element;
a device opening distal to the sampling port;
a device lumen extending from the device opening toward the second portion; and
the second shaft is configured to slidingly extend through the device lumen such that the distal end portion extends through the device opening.

17. The system of example 16, further comprising an analyzer configured to analyze a biological sample from the patient for a biological parameter that changes in response to modulating the nerves.

18. The system of example 17 wherein:
the analyzer is operably connected to the second portion; and
the sampling lumen extends from the sampling port along the shaft to the analyzer.

19. The system of example 17 or example 18, further comprising a handle coupled to the second portion, wherein the analyzer is carried by the handle.

20. The system of any one of examples 17 to 19 wherein the analyzer includes an indicator configured to indicate a status of the biological parameter, a status of modulation of the nerves based on the biological parameter, or both.

21. A system, comprising:
an intravascular catheter having a handle at a proximal portion, a neuromodulation and
sampling assembly at a distal portion, and an elongated shaft therebetween, the neuromodulation and sampling assembly including—
a neuromodulation element configured to modulate renal nerves,
a sampling element proximal to the neuromodulation element and configured to collect a renal blood sample, the sampling element having—
a sampling port;
a sampling lumen extending from the sampling port along the shaft to the handle;
an occlusion element proximal to the sampling element, the occlusion element having—
a balloon;
an inflation opening within the balloon;
an inflation lumen extending from the inflation opening toward the handle;
a console operably connected to the handle, the console configured to supply energy to the neuromodulation element; and
an analyzer configured to detect a concentration of a biomarker within the renal blood sample, the concentration corresponding to a degree of modulation of the renal nerves.

22. A method, comprising:
positioning a neuromodulation element at a treatment site within or otherwise proximate to a renal vasculature of a patient;
activating the neuromodulation element to modulate renal nerves of the patient;
expanding an occlusion member at an occlusion site within the renal vasculature after activating the neuromodulation element;
collecting a blood sample from a portion of the renal vasculature distal to the occlusion site after expanding the occlusion member; and
analyzing the blood sample for a biological parameter that changes in response to modulating the nerves.

23. The method of example 22 wherein:
collecting a blood sample comprises collecting a second blood sample;
the method further comprises collecting a first blood sample from a portion of the renal vasculature before activating the neuromodulation element; and
analyzing the blood sample comprises analyzing the first blood sample and the second blood sample.

24. The method of example 22 wherein collecting the blood sample includes conveying the blood sample from a sampling port within the renal vasculature along a sampling lumen to a portable container, and the method further comprises moving the container to a blood analysis unit configured to analyze the blood sample.

25. The method of example 22 wherein:
expanding the occlusion member includes inflating a balloon to fully occlude a renal artery of the renal vasculature; and
collecting the blood sample includes—
collecting a first quantity of blood after inflating the balloon,
partially deflating the balloon after collecting the first quantity of blood,
reinflating the balloon after partially deflating the balloon such that the balloon fully occludes the renal artery,
collecting a second quantity of blood after reinflating the balloon; and
combining the first and second quantities of blood to form the blood sample.

26. The method of example 22 wherein:
analyzing the blood sample includes taking a measurement of the biological parameter;
activating the neuromodulation element occurs at a first time; and
the method further comprises activating the neuromodulation element at a second time in response to the measurement.

27. The method of example 26 wherein the second time is less than about 15 minutes after the first time.

28. A system, comprising:
an elongated shaft including a distal portion configured for intraluminal delivery to an artery of a human patient;
a neuromodulation and sampling assembly connected to the shaft via the distal portion, the assembly including—
an energy delivery element configured to modulate nerves at least proximal to an artery of a patient,
a sampling port configured to intravascularly obtain a biological sample from the patient at or near the treatment site;
an analyzer operably coupled to the shaft and configured to receive at least a portion of the biological sample and indicate a status of the biological sample and/or a status of modulation of the nerves based on the biological sample.

29. The system of example 28 wherein the neuromodulation and sampling assembly further includes an occlusion member extending around a portion of the shaft proximal to the sampling port.

30. The system of example 28 or example 29, further including a sampling lumen extending from the sampling port toward a proximal portion of the elongated shaft.

31. The system of example 30 wherein the sampling lumen is operably connected to a negative pressure source.

32. The system of example 30 or example 31 wherein the sampling lumen includes a one-way valve.

33. The system of any one of examples 28 to 32 wherein the neuromodulation and sampling assembly includes a plurality of sampling ports interspersed with a plurality of energy delivery elements.

V. Conclusion

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system, comprising:
   an elongated shaft including a distal portion configured for intraluminal delivery to an artery of a patient;
   a neuromodulation and sampling assembly coupled to the distal portion of the elongated shaft, the neuromodulation and sampling assembly including:
   an occlusion member extending around a portion of the elongated shaft,
   an energy delivery element configured to modulate nerves at least proximal to the artery of the patient,
   a sampling port within an outer surface of the elongated shaft and distal to the occlusion member, the sampling port being configured to intravascularly obtain a biological sample from the patient at or near a treatment site, and
   a sampling lumen in fluid communication with the sampling port and having a one-way valve or seal configured to prevent the biological sample from contaminating a negative pressure source; and
   an analyzer coupled to the elongated shaft and configured to receive at least a portion of the biological sample obtained from the sampling port via the sampling lumen and detect a change in a level or activity of a target biomarker within the biological sample following modulation of the nerves using a capture agent or a detection agent.

2. The system of claim 1, wherein the sampling lumen extends from the sampling port toward a proximal portion of the elongated shaft.

3. The system of claim 2, wherein the sampling lumen is operably connected to and in fluid communication with the negative pressure source.

4. The system of claim 3, wherein the energy delivery element includes a first energy delivery element, and wherein the neuromodulation and sampling assembly further includes a plurality of additional energy delivery elements, and a plurality of sampling ports interspersed with the plurality of additional energy delivery elements.

5. The system of claim 1, further comprising a guide wire lumen within the elongated shaft, wherein the neuromodulation and sampling assembly is configured for guide wire delivery to the artery of the patient.

6. The system of claim 1, wherein the energy delivery element includes a first energy delivery element, and wherein the neuromodulation and sampling assembly further includes a plurality of additional energy delivery elements spaced apart from the first energy delivery element and each another, and wherein the energy delivery elements are configured to simultaneously deliver radio frequency (RF) energy to the nerves.

7. The system of claim 1, wherein:
   the energy delivery element has a delivery state and a deployed state; and
   at least a portion of the energy delivery element is helical in the deployed state.

8. The system of claim 1, wherein the energy delivery element comprises a single electrode.

9. The system of claim 1, wherein the distal portion of the elongated shaft is configured for intraluminal delivery to a renal blood vessel of the patient.

10. The system of claim 1, wherein the distal portion of the elongated shaft is configured for intraluminal delivery to a renal artery of the patient.

11. The system of claim 1, wherein the occlusion member is a compliant balloon.

12. The system of claim 1, further comprising a handle coupled to a proximal portion of the elongated shaft, and wherein the analyzer is carried by the handle.

13. The system of claim 1, wherein the detection agent is a substrate for the target biomarker or an enzyme or catalytic antibody for which the target biomarker is the substrate.

14. The system of claim 1, wherein the capture agent is an agent that binds to the target biomarker or binds to an enzymatic product or byproduct of the target biomarker.

15. A catheter, comprising:
   an elongated shaft including a distal portion configured for intravascular delivery to a treatment site within a renal blood vessel of a patient, and a proximal portion configured to be extracorporeally positioned while the distal portion is within the renal blood vessel;
   a neuromodulation and sampling assembly coupled at the distal portion of the elongated shaft, the neuromodulation and sampling assembly including:
   an occlusion member extending around a portion of the elongated shaft,
   a neuromodulation element configured to modulate renal nerves of the patient, and a sampling port within an outer surface of the elongated shaft, wherein the sampling port is distal to the occlusion member and configured to intravascularly obtain a blood sample from the patient at or near the treatment site;

a sampling lumen in fluid communication with the sampling port and having a one-way valve or seal configured to prevent the blood sample from contaminating a negative pressure source; and an analyzer in fluid communication with the sampling port via the sampling lumen and configured to receive at least a portion of the blood sample from the sampling port, the analyzer being configured to detect a change in a level or activity of a target biomarker within the blood sample following modulation of the renal nerves using a capture agent or a detection agent.

16. The catheter of claim 15, wherein the neuromodulation element has a delivery arrangement and a deployed arrangement, wherein at least a portion of the neuromodulation element is helical in the deployed arrangement.

17. The catheter of claim 15, wherein the analyzer further comprises one or more of the following: a physiochemical transducer, a piezoelectric transducer, and a processing device having processing circuitry.

18. The catheter of claim 15, further comprising a handle assembly at the proximal portion of the elongated shaft, and wherein the analyzer is incorporated into the handle assembly.

19. The catheter of claim 18, wherein the handle assembly further comprises an indicator configured to provide an auditory or a visual indication related to processing of the blood sample by the analyzer.

* * * * *